US008496661B2

(12) United States Patent
Moore et al.

(10) Patent No.: US 8,496,661 B2
(45) Date of Patent: Jul. 30, 2013

(54) SYSTEM AND METHOD FOR MICRO-INVASIVE TRANSFACET LUMBAR INTERBODY FUSION

(75) Inventors: Shawn Moore, Topeka, KS (US); Stephen M. Pope, Lenexa, KS (US); Cory Buckingham, Littleton, CO (US); Nick Tobaben, Topeka, KS (US); Sally Mayer, Lawrence, KS (US); Diana Marcolino Underwood, Lawrence, KS (US)

(73) Assignee: Omni Surgical LLC, Austin, TX (US)

( * ) Notice: Subject to any disclaimer, the term of this patent is extended or adjusted under 35 U.S.C. 154(b) by 603 days.

(21) Appl. No.: 12/609,752

(22) Filed: Oct. 30, 2009

(65) Prior Publication Data

US 2010/0114179 A1 May 6, 2010
US 2010/0274297 A2 Oct. 28, 2010

Related U.S. Application Data

(60) Provisional application No. 61/110,822, filed on Nov. 3, 2008.

(51) Int. Cl.
*A61B 17/70* (2006.01)
(52) U.S. Cl.
USPC ........................................................ 606/86 A
(58) Field of Classification Search
USPC ........................................................ 606/86 A
See application file for complete search history.

(56) References Cited

U.S. PATENT DOCUMENTS

| 2003/0073998 | A1* | 4/2003 | Pagliuca et al. | 606/61 |
| 2004/0215190 | A1* | 10/2004 | Nguyen et al. | 606/61 |
| 2005/0080418 | A1* | 4/2005 | Simonson et al. | 606/61 |
| 2005/0251139 | A1* | 11/2005 | Roh | 606/61 |
| 2006/0036244 | A1* | 2/2006 | Spitler et al. | 606/61 |
| 2006/0079894 | A1* | 4/2006 | Colleran et al. | 606/61 |
| 2006/0247630 | A1* | 11/2006 | Iott et al. | 606/61 |
| 2007/0233079 | A1* | 10/2007 | Fallin et al. | 606/61 |
| 2007/0299444 | A1* | 12/2007 | DiPoto et al. | 606/61 |
| 2008/0039841 | A1* | 2/2008 | Casutt et al. | 606/61 |
| 2008/0077138 | A1* | 3/2008 | Cohen et al. | 606/61 |
| 2009/0143828 | A1* | 6/2009 | Stad et al. | 606/86 A |
| 2010/0004695 | A1* | 1/2010 | Stad et al. | 606/86 A |

OTHER PUBLICATIONS

Mick Perez-Cruet, MD, MS, "Versatility: PathFinder(R) Minimally Invasive Spine Instrumentation System" May 2007.

(Continued)

*Primary Examiner* — Eduardo C Robert
*Assistant Examiner* — Julianna N Harvey
(74) *Attorney, Agent, or Firm* — David O. Simmons

(57) ABSTRACT

Spinal surgery systems are provided. In one embodiment, a system includes threaded caps and screw assemblies. Each assembly includes a cannulated and threaded screw having upper and lower ends, a polyaxial head permanently fixed to the screw upper end in a ball-and-socket engagement, and an extension portion fixed to the head wherein extension portion movement causes the head to move in concert. Each head has a receiving area for engaging a rod and a threaded area for receiving one of the caps after the rod is engaged in the receiving area. Each extension portion has: (a) two arms spaced apart such that the arms are on opposite sides of the polyaxial head receiving area; and (b) at least one point of weakness such that forcing the arms away from one another causes the extension portion to divide at the point of weakness and separate the extension portion from the head.

11 Claims, 26 Drawing Sheets

OTHER PUBLICATIONS

Depuy Spine press release titled "Depuy Spine Launches New Minimally Invasive Spine Surgery Product Line" and dated Mar. 11, 2005.
About the METRx(R) System, accessible at http://www.lessinvasivespine.com/metrx-system.html and dated Apr. 3, 2008.
About the CD Horizon(R) Sextant(R) Spinal System, accessible at http://www.lessinvasivespine.com/sextant-system.html and dated Apr. 3, 2008.
About the METRx(R) X-Tube(R) Retraction System, accessible at http://www.lessinvasivespine.com/xtube-system.html and dated Apr. 3, 2008.
About the Mast Quadrant(TM) Retractor System, accessible at http://www.lessinvasivespine.com/quadrant-system.html and dated Apr. 15, 2008.
CD Horizon(R) Spire(TM) Stabilization System, accessible at http://www.lessinvasivespine.com/spire-system.html and dated Apr. 17, 2008.
Anterior Cervical Discectomy and Fusion accessible through Spineline Procedures website and dated 2005.
Anterior Cervical Corpectomy accessible through Spineline Procedures website and dated 2005.
Posterior Cervical Decompression and Fusion accessible through Spineline Procedures website and dated 2005.
Lumbar Laminectomy and Discectomy accessible through Spineline Procedures website and dated 2005.
Anterior Lumbar Interbody Fusion (ALIF) accessible through Spineline Procedures website and dated 2005.
Posterior Lumbar Interbody Fusion accessible through Spineline Procedures website and dated 2005.
Transforaminal Interbody Fusion (TLIF) accessible through Spineline Procedures website and dated 2005.

* cited by examiner

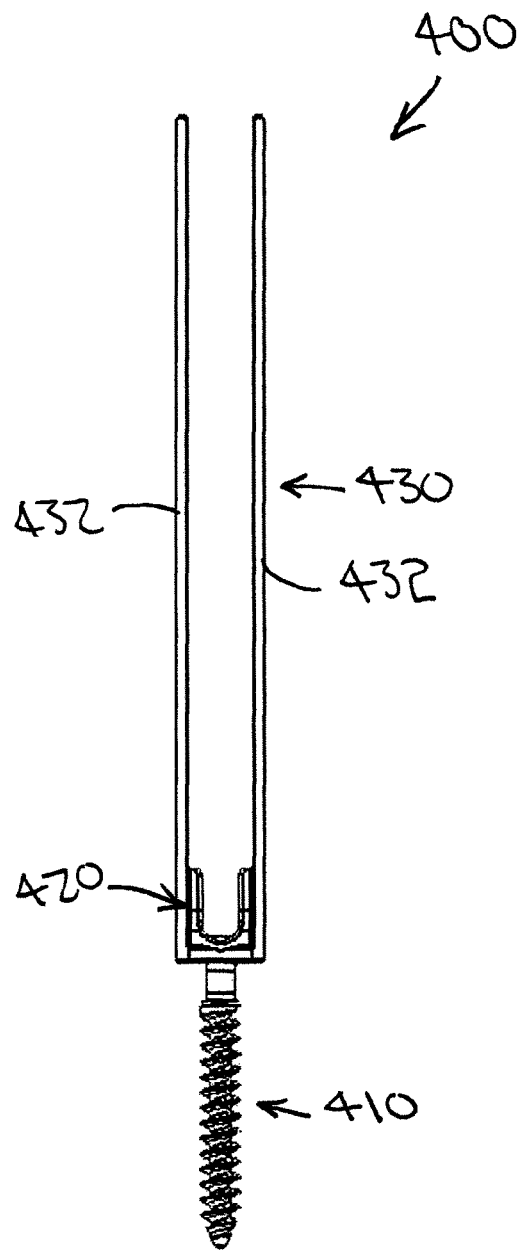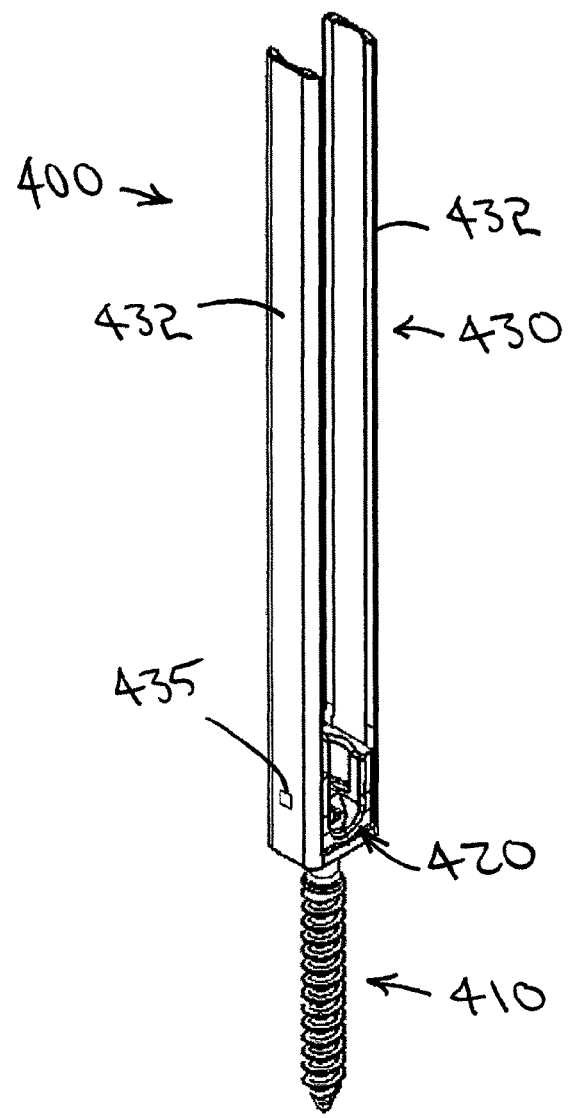
FIG. 10
FIG. 11

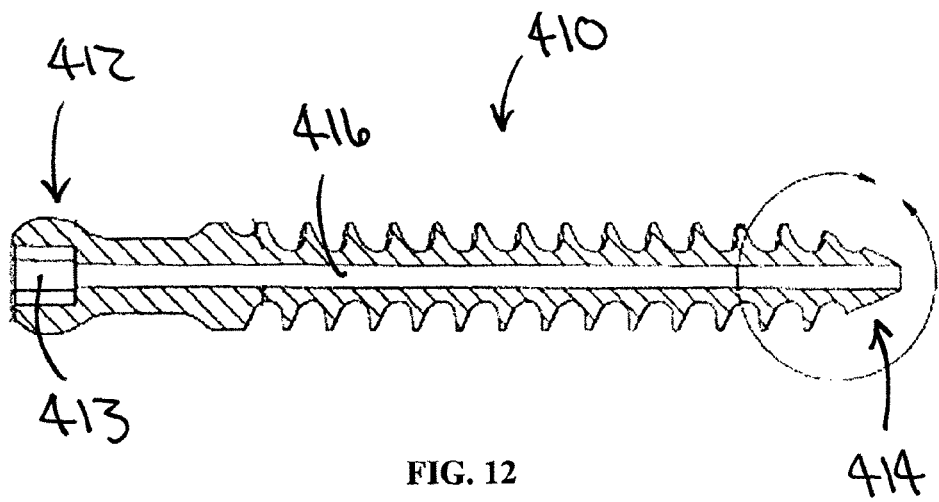
FIG. 12
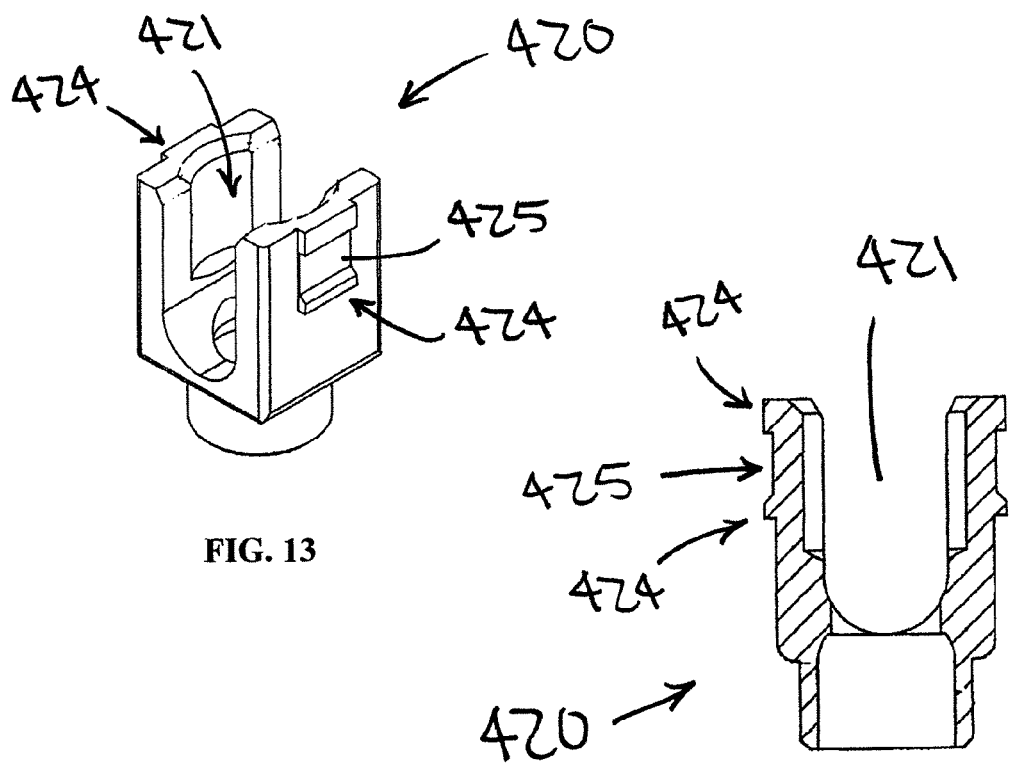
FIG. 13
FIG. 14

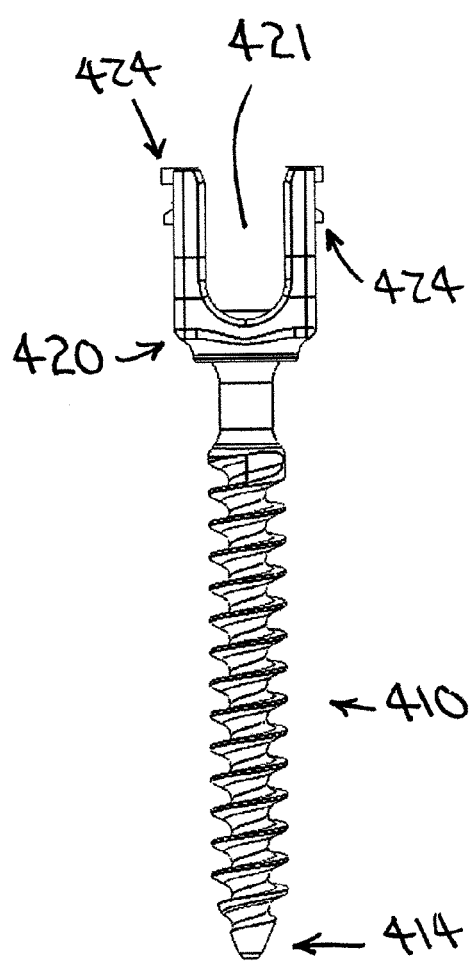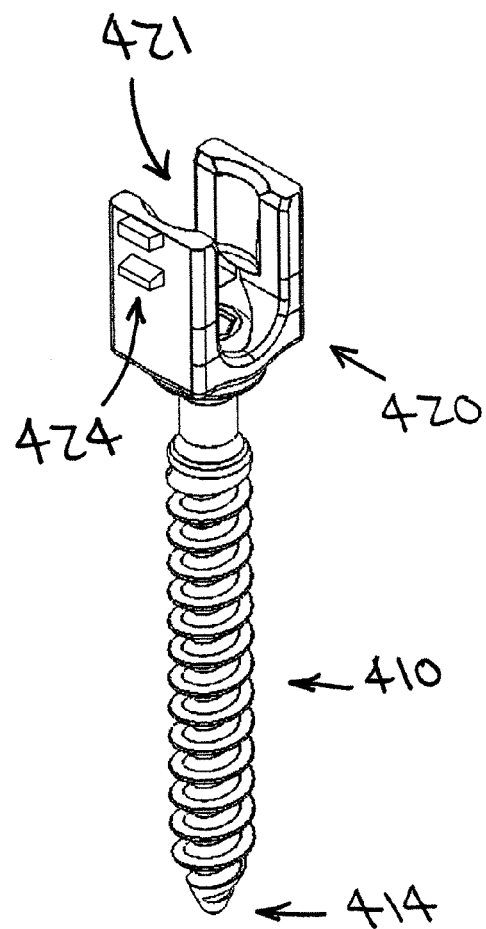
FIG. 15
FIG. 16

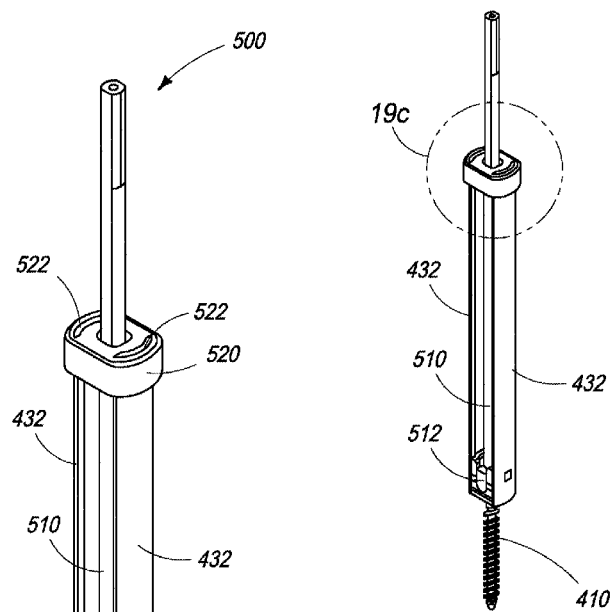
FIG. 19a
FIG. 19b
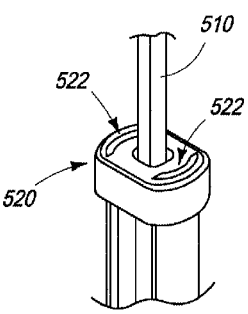
FIG. 19c

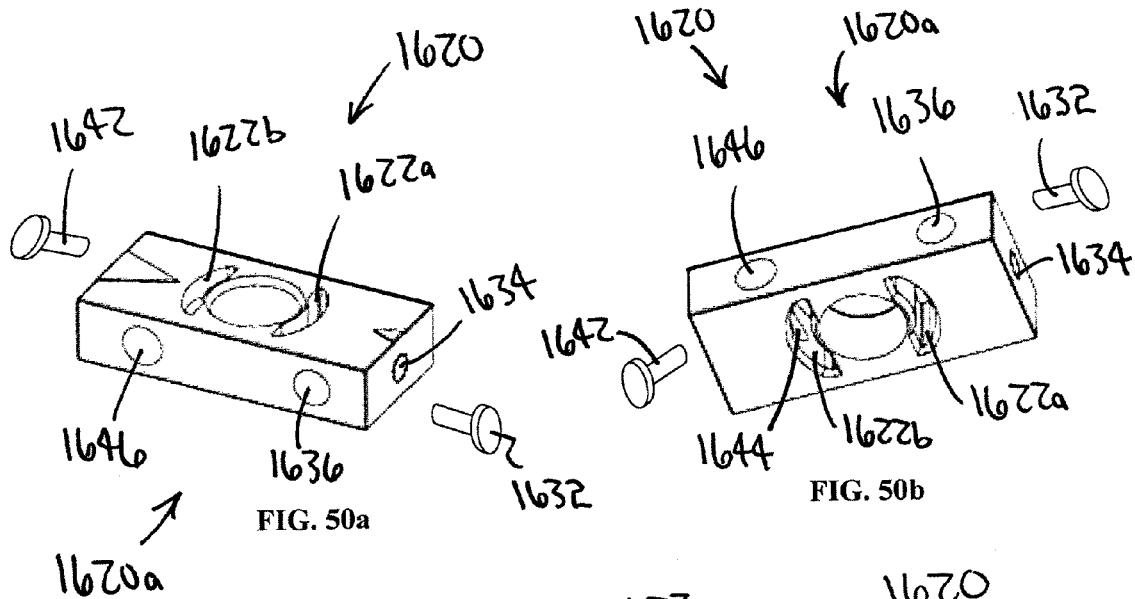
FIG. 50a
FIG. 50b
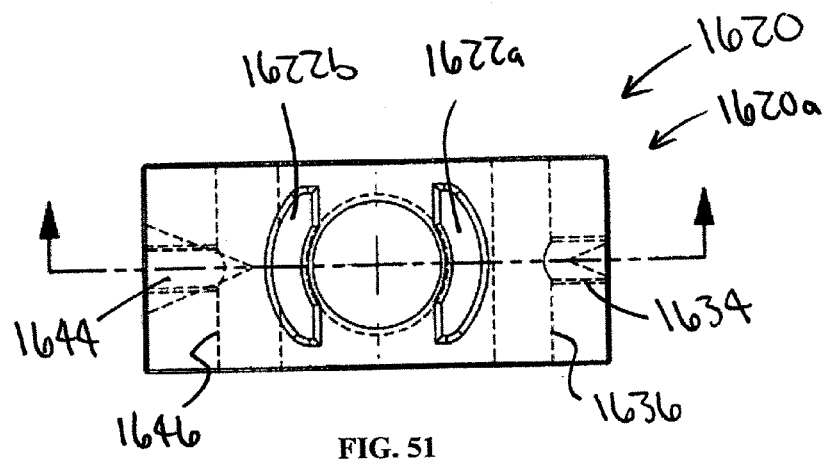
FIG. 51
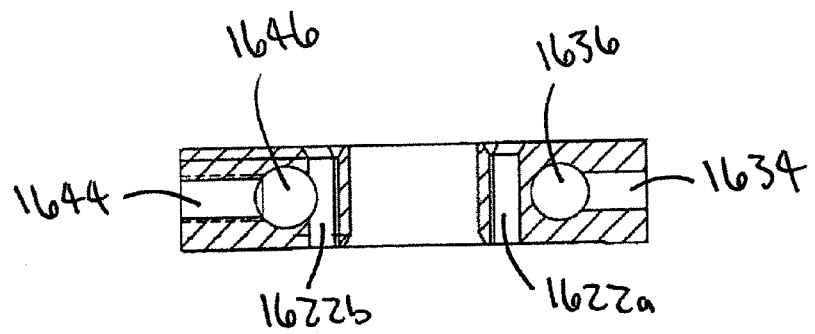
FIG. 52

SYSTEM AND METHOD FOR MICRO-INVASIVE TRANSFACET LUMBAR INTERBODY FUSION

RELATED APPLICATIONS

This application claims priority to U.S. Provisional Patent Application Ser. No. 61/110,822, filed Nov. 3, 2008, the disclosure of which is incorporated herein by reference.

FIELD

The present application relates to equipment for, and methods of, performing surgeries. In particular, the present application relates to implantable devices for decompressing, fusing, and stabilizing the spine and methods and equipment for implanting such devices during spinal surgery.

BACKGROUND

Prior art surgical procedures on the spine are substantially invasive. Even procedures currently marketed as "minimally-invasive" typically require incisions that are several inches long. Because smaller incisions and less invasive procedures would result in shorter hospitalizations and faster patient recovery, a procedure that is truly minimally invasive (or "micro-invasive") is desirable. It is estimated that using the equipment and procedures set forth herein could shorten typical post-operative hospital stays from three to five days to one day for spinal stabilization and spinal fusion procedures.

Nevertheless, the prior art minimally-invasive spinal procedures have increased in popularity over the course of the past decade. Compared to the open techniques that came before them, these prior art minimally-invasive procedures allow patients to experience shorter hospital stays, faster post-operative recoveries, and an earlier return to work. These procedures were initially limited to simple decompressive procedures. Over the past few years, however, surgeons have begun to expand the applications of these systems to include spinal stabilization and spinal fusion procedures.

FIG. 1 shows two generic vertebrae 100, and FIG. 2 shows a top view of FIG. 1. The front (or "anterior") portion of the vertebra 100 is the body 102. The bodies 102 of adjacent vertebrae 100 are typically separated by an intervertebral disk 154. Posteriorly, the body 102 is joined by a left pedicle 104 and right pedicle 106 to the lamina 108. The lamina 108 joins a spinous process 114 that generally serves for muscle and ligamentous attachments. Transverse processes 110 and 112 project laterally from the junction of the respective pedicle 104, 106 and the lamina 108 and also serve for muscle and ligamentous attachments. A supraspinous ligament attaches the spinous processes 114 of adjacent vertebrae 100 to provide stability to the spinal column.

The lamina 108, pedicles 104, 106, and body 102 surround a passageway known as the vertebral foramen 116. The vertebra 100 also has articular processes 118 that extend above and below the vertebra 100 to interact with adjacent vertebra 100; these interactions are known as facet joints.

While the parts of vertebrae 100 shown in FIG. 1 and FIG. 2 are common to most vertebrae 100 of the spinal column, details of anatomy differ with position of the vertebra 100 in the spinal column. For example, the vertebral body 102 is wider at lower levels of the spinal column, such as the lumbar region, than in vertebrae of the cervical spine; this provides greater weight-bearing capability at the lower levels. The body 102 of each vertebra is located anterior to the lamina 108 and spinous process 114. The spinal cord—or for lumbar vertebrae 100 its caudal extension, the cauda equina—passes through the vertebral foramen 116. Also found within the vertebral foramen 116 exiting the spinal cord are dorsal and ventral roots, arteries, veins, and a posterior longitudinal ligament 120 that attaches each vertebra 100 to its adjacent vertebrae 100. In addition, there is an anterior longitudinal ligament 122 that attaches each vertebra 100 to its adjacent vertebrae 100. Motor and sensory nerves exit the spinal canal together at a space between pedicles 106, 104 of adjacent vertebrae 100 known as intervertebral or neural foramina.

As a subject ages, or suffers injury, various disease processes may narrow, or impinge on, the spinal canal defined by successive vertebral foramens 116 such that less space is available for the spinal cord, nerve roots, and other tissues. Among these disease processes may be bulging or rupture of an intervertebral disk 154 that impinges on the spinal canal, tumors, abscesses, ligamentous hypertrophy, spondylolisthesis, ossification of the posterior longitudinal ligament, bone spur formation, etc. Whenever the spinal canal, defined by successive vertebral foramina 116, is effectively narrowed by a disease process impinging on the spinal cord, cauda equina, or nerve root, function may be impaired. This may result in symptoms of numbness, weakness, ataxia, impotence, incontinence, pain, and even paralysis. In some subjects, it is necessary to surgically decompress the neural elements to prevent further damage and provide relief of symptoms. Surgical decompression often requires a laminectomy to provide additional room for the spinal canal, which involves cutting through the lamina 108 on both sides of the spinous process 114 and subsequently removing this segment.

Further, damage to (including fractures) or diseases (including arthritis) of the vertebral body 102, the facet joints 118 between vertebrae 100, or the intervertebral disks 154 between adjacent vertebral bodies 102 may require surgical intervention. And in some patients, vertebral bodies 102 may be anteriorly displaced in relation to each other. This may result from fractures or diseases of the facet joints 118, or from defects in the pars interarticularis, and is known as spondylolisthesis.

A known surgical stabilization technique is spinal fusion with instrumentation; this has traditionally been done using an open surgical technique where the spinal column is approached from the front through the abdomen to gain access to the vertebral body 102, and/or from the back. In this surgery, an intervertebral disk 154 between two vertebrae 100 is often removed and replaced with an implant that is typically made of bone, metal, or another appropriate substance. This type of surgery is known as an interbody fusion. The implant provides the necessary matrix to allow bone growth and healing to fuse the adjacent vertebrae 100. Posterolateral fusions can also be performed between the transverse processes 110 and 112 of adjacent vertebrae. Other repairs to the vertebral body 102 may also be done.

After the matrix for fusion has been established (i.e. via posterolateral and/or interbody fusion), instrumentation is often utilized to stabilize the spinal column and promote fusion (arthrodesis) by preventing micromotion of the instrumented adjacent vertebra 100. Several different forms of instrumentation have been developed in the past. However, biomechanical studies have proven that pedicle screws provide the most effective form of lumbar spinal instrumentation with the highest pull-out strength. Pedicle screws are placed from a posterior approach at the junction of the transverse process 110, 112 and facet 118. These screws are then passed through the pedicle 104, 106 into the vertebral body 102. The pedicle screws of adjacent vertebral bodies 102 are then attached to rods, and this construct provides stabilization to the fused segment by preventing micromotion.

Conventional open surgical techniques typically utilize larger incisions, as direct visualization of the vertebral structures is required, and occasionally require both anterior and posterior approaches to the spine. Prior art minimally-invasive techniques, as noted above, typically utilize incisions that are several inches long, which results in hospitalizations and recoveries that are marginally better than comparable open surgical techniques. Micro-invasive systems and methods, such as those set forth herein, may result in shorter hospitalizations, faster post-operative recoveries, less narcotic dependence, and earlier return to work than both open and prior art minimally-invasive techniques.

SUMMARY

Systems for use in performing spinal surgery are provided herein. In one embodiment, a system includes at least two threaded caps and at least two screw assemblies. Each assembly includes a cannulated and threaded screw having upper and lower ends, a polyaxial head permanently fixed to the screw upper end in a ball-and-socket engagement, and an extension portion fixed to the head wherein movement of the extension portion causes the head to move in concert. Each head has a receiving area for engaging a rod and a threaded area for receiving one of the caps after the rod is engaged in the receiving area such that the rod is sandwiched by the polyaxial head and the cap. Each extension portion has: (a) two arms spaced apart such that the arms are on opposite sides of the polyaxial head receiving area; and (b) at least one point of weakness such that forcing the arms away from one another causes the extension portion to divide at the point of weakness and separate the extension portion from the head.

In another embodiment, a system includes for use in performing spinal surgery includes a rod, at least two threaded caps, and at least two screw assemblies. Each screw assembly includes a cannulated and threaded screw having upper and lower ends, a polyaxial head permanently fixed to the screw upper end in a ball-and-socket engagement, and an extension portion attached to the polyaxial head wherein movement of the extension portion causes the polyaxial head to move in concert. Each polyaxial head has a receiving area for engaging the rod and a threaded area for receiving one of the caps after the rod is engaged in the receiving area such that the rod is sandwiched by the polyaxial head and the cap. Each extension portion has: (a) first and second arms configured to pass the rod therebetween and guide the rod to the polyaxial head receiving area; and (b) at least one point of weakness such that forcing the arms away from one another causes the extension portion to divide at the point of weakness and separate the extension portion from the polyaxial head.

BRIEF DESCRIPTION OF THE DRAWINGS

FIG. 5b is a side view of the port of FIG. 5a.

FIG. 5c is another perspective view of the port of FIG. 5a.

FIG. 10 is a front view of the screw assembly of FIG. 9.

FIG. 11 is a perspective view of the screw assembly of FIG. 10.

FIG. 12 is a sectional view of a pedicle screw from the screw assembly of FIG. 10.

FIG. 13 is a perspective view of a polyaxial head from the screw assembly of FIG. 10.

FIG. 14 is a sectional view of the polyaxial head of FIG. 13.

FIG. 15 is front view of the pedicle screw and the polyaxial head of FIG. 10.

FIG. 16 is perspective view of the pedicle screw and the polyaxial head of FIG. 15.

FIG. 19a is perspective view of a screwdriver, according to an embodiment, in use with the screw assembly of FIG. 10.

FIG. 19b is another perspective view of the screwdriver and the screw assembly of FIG. 19a.

FIG. 19c is a partial view taken from FIG. 19b.

FIG. 50a is a perspective view of one receiving member of the alignment tool of FIG. 48.

FIG. 50b is another perspective view of the receiving member of FIG. 50a.

FIG. 51 is a top view of the receiving member of FIG. 50a.

FIG. 52 is a sectional view of the receiving member of FIG. 50a.

FIG. 53b is another perspective view of the receiving member of FIG. 53a.

FIG. 54 is a top view of the receiving member of FIG. 53a.

FIG. 55 is a sectional view of the receiving member of FIG. 53a.

DETAILED DESCRIPTION

The equipment and methods set forth herein may allow spine surgeons to perform posterior lumbar decompressions (e.g., laminectomies, microdiscectomies, facetectomies, and lumbar interbody fusions) in addition to posterior pedicle screw instrumentation through a small, single incision. Notably, the disclosed equipment and methods may allow spine surgeons to perform a decompressive laminectomy from a posterior approach through smaller incisions than possible with prior art systems.

Figure 1:
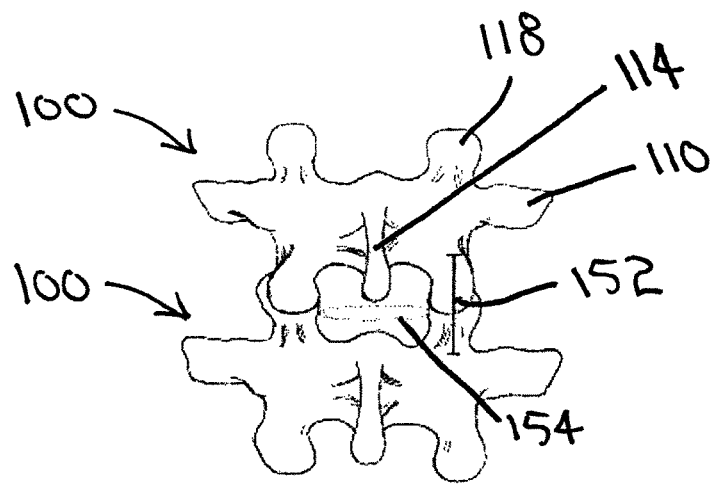
FIG. 1 is a posterior view of a pair of generic vertebrae.
Figure 2:
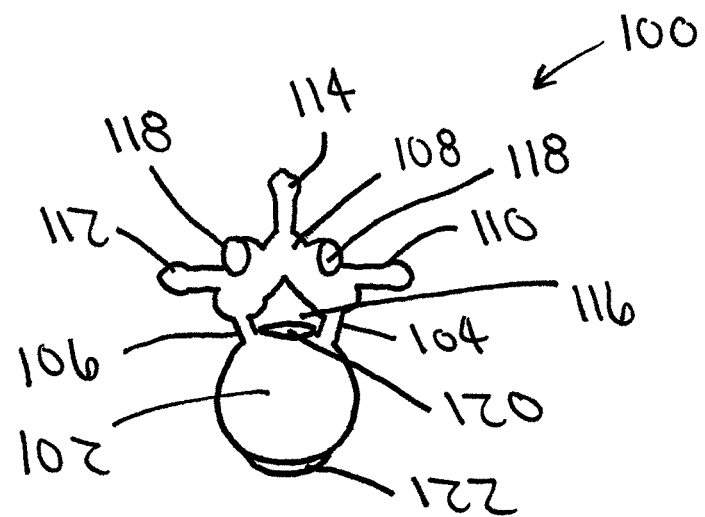
FIG. 2 is a top view of one of the generic vertebra from FIG. 1.
Figure 3:
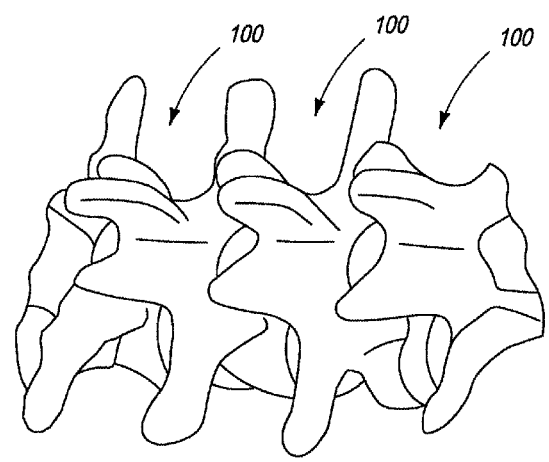
FIG. 3 is an oblique view of the posterolateral spinal column.
Figure 4:
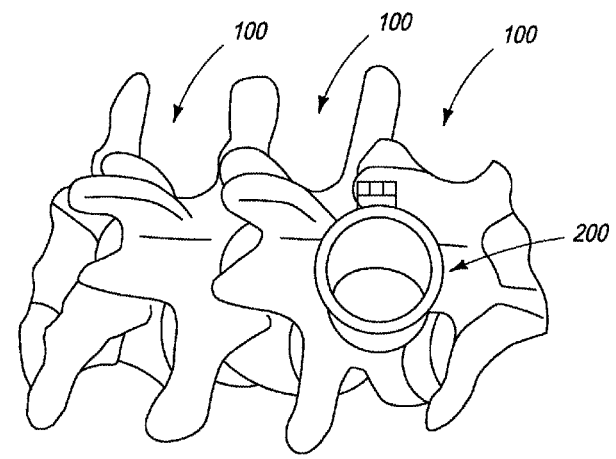
FIG. 4 shows a port, according to an embodiment, placed over a facet joint from FIG. 3.

A minimally invasive fusion procedure (and equipment used) according to one embodiment is shown and described with reference to FIGS. 1 through 46 of the accompanying drawings. As set forth above, FIGS. 1 and 2 show generic vertebrae 100. FIG. 3 similarly shows generic vertebrae 100. In FIG. 4, with the aid of fluoroscopy, a port 200 has been placed percutaneously through the patient's skin at a facet joint 118. The incision location is shown in FIG. 1 at line 152.

Figure 5A:
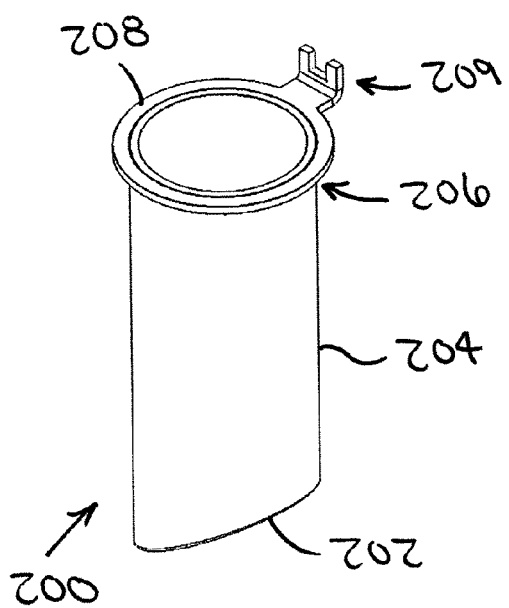
FIG. 5a is a perspective view of the port of FIG. 4.
Figure 5B:
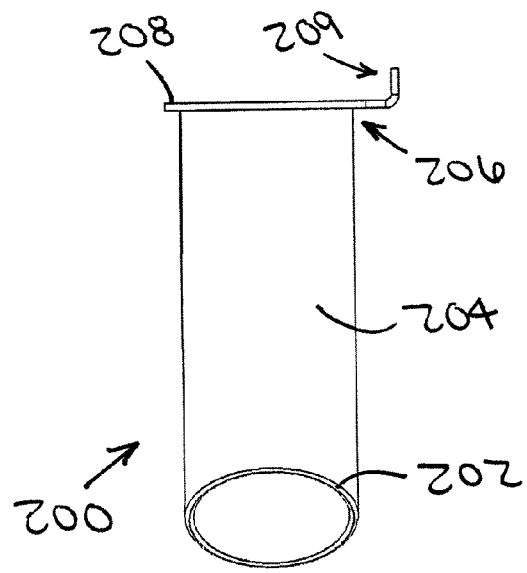
Figure 5C:
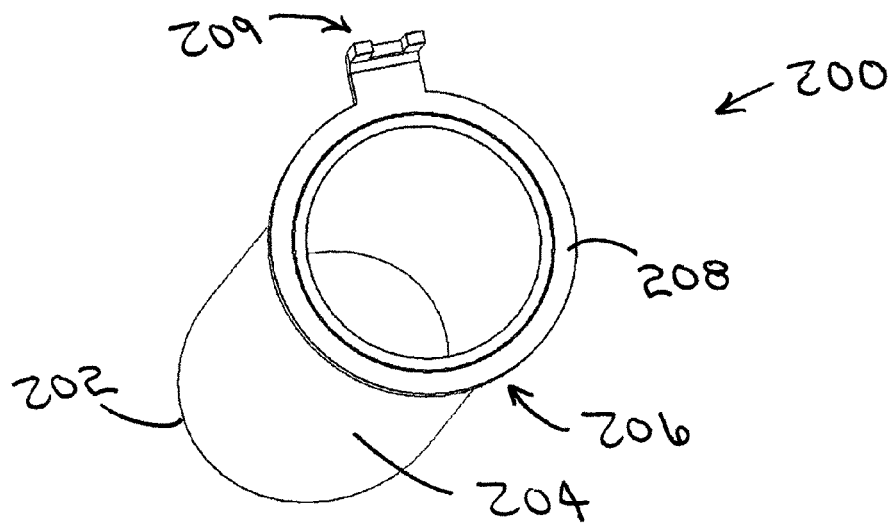
Figure 6:
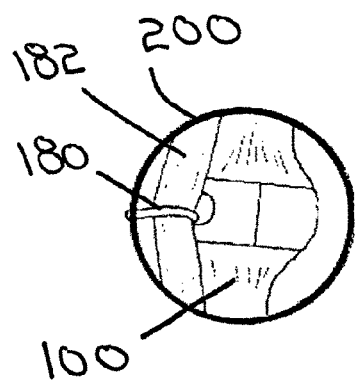
FIG. 6 is an illustration of a view through the port of FIG. 4, showing retraction of a descending nerve root.
Figure 7:
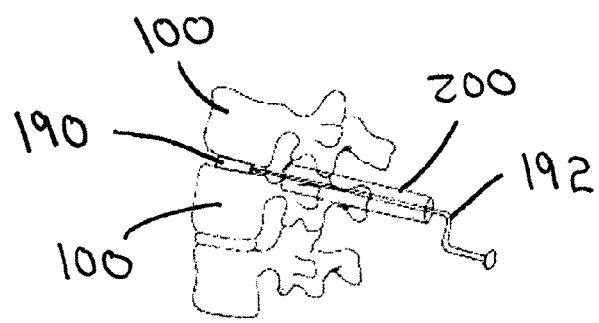
FIG. 7 illustrates placement of an interbody fusion device between adjacent vertebrae through the port of FIG. 4.
Figure 8:
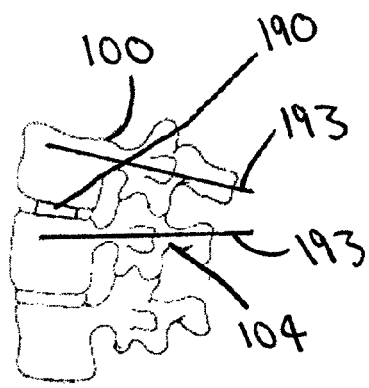
FIG. 8 illustrates placement of K-wires within pedicles of adjacent vertebrae.

The port 200 is shown in detail in FIGS. 5a through 5c. Unlike prior art ports, which are tubular and have upper and lower ends that are generally perpendicular to the sidewall, the port 200 has a lower end 202 that is not perpendicular to sidewall 204. Though various angles may be appropriate, an angle between twenty and forty degrees to the horizon, and preferably an angle of approximately thirty degrees, may be most desirable. This angled configuration may allow the lower end 202 of the port 200 to be simultaneously positioned along the facet 118 and adjacent lamina 108 of the vertebrae 100. This distinguishes the port 200 from prior art by allowing the surgeon to perform a facetectomy/microdiscectomy concomitant to performing a laminectomy through the same approach for spinal decompression.

In addition, the port 200 includes a lip (sometimes referred to herein as "rim") 208 at an upper end 206. The rim 208 provides an advantage over the prior art in that a nerve root retractor 180 (shown in FIG. 6 holding nerve roots 182 out of the way) and/or other equipment may be attached to the rim 208, allowing hands-free operation of the attached equipment. And, as shown in FIGS. 5a through 5c, an engagable portion 209 may extend upwardly from the lip 208. Though not shown in the drawings, an arm may attach to the engagable portion 209 and secure the port 200 to the bed to stabilize the port 200. It should be understood that other engagable configurations may additionally, or alternately, be used.

While various materials and configurations would be appropriate for the port 200, in one currently preferred embodiment, the port 200 is constructed of titanium, the sidewall 204 has a wall thickness of about one millimeter, and the rim 208 has an outer diameter that is about four millimeters greater than the inner diameter. The inner diameter of the port 200 may vary in increments (e.g., two millimeter increments, from 16 to 26 millimeters inner diameter), allowing for use in different patients with different pathology. Accordingly, multiple ports 200 may be present to allow the appropriately-sized port 200 to be selected for a given procedure. In some embodiments, the port 200 may contain a radiopaque ring at the tip for visualization by intraoperative fluoroscopy, while the port itself is radiolucent; the surgeon may thus determine exactly where the port 200 is docked in the patient by imaging this radiopaque ring.

Returning now to FIG. 4, after the port 200 is secured in place, the facet joint 118 and lamina 108 may be resected using conventional tools and a microscope. Once the lamina 108 is removed, the contra lateral lamina may be removed as well by under-cutting the spinous process. Removal of the lamina 108 allows the spinal cord to be decompressed centrally, and removal of the facet 118 and intervertebral disc 154 allows the nerve root to be decompressed.

After the necessary portions are removed, adjacent vertebrae 100 are fused together by a spinal fusion device 190 (FIG. 7), which is well known in the art, and may include such devices as a bony implant, a PEEK (polyether keytone) implant, bone morphogenic protein, a titanium cage, et cetera. The fusion device 190 is attached to an insertion tool 192 placed in the port 200 and wedged into the disc space using fluoroscopy. Once the fusion device 190 is appropriately positioned, hemostasis is obtained and the port 200 is removed.

As time passes, bone growth will result in spinal fusion as the spinal fusion device 190 is incorporated into the end plates of the bodies 102 of adjacent vertebrae 100, fusing both vertebrae 100 into a single bony unit. Stabilization, which in this case involves placement of pedicle screw instrumentation, significantly improves arthrodesis rates and provides stability in patients with instability, such as may result from fractures or spondylolisthesis.

Pedicle screw instrumentation begins with placement of standard Jamshidi needles (not shown) into adjacent pedicles 104 (or pedicles 106) with use of intraoperative fluoroscopy. This is done through the patient's skin, as the port 200 has been removed. Bone penetrating, stainless steel, "K-wires" 193 (FIG. 8) are then passed through the Jamshidi needles into the pedicles 104 (or the pedicles 106) of each vertebra 100 and are advanced into the vertebral bodies 102 of the vertebrae 100 above and below the interbody fusion device 190. Though the patient's skin is not shown in the accompanying drawings, it should be understood that the K-wires 193 stick out through the skin percutaneously.

Figure 9:
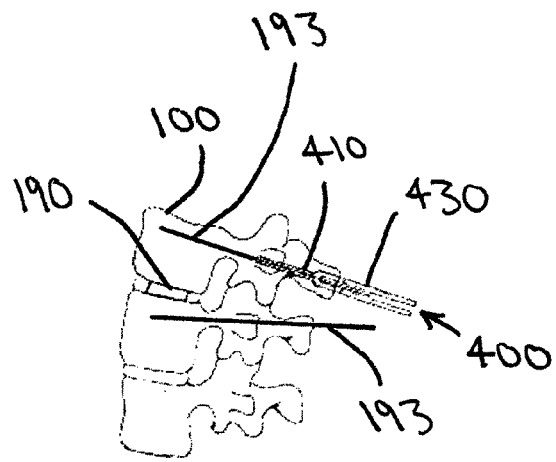
FIG. 9 illustrates percutaneous placement of a screw assembly, according to an embodiment.

Next, a pedicle screw assembly 400 is inserted over each K-wire 193 and advanced into the pedicle 104 (or the pedicle 106) and into the vertebral body 102. FIG. 9 shows one screw assembly 400 in place, and the screw assembly 400 is shown in detail in FIGS. 10 through 18. A screwdriver 500 for use in placing the screw assembly 400 is shown in FIGS. 19a through 19c and described below.

The screw assembly 400 includes a pedicle screw 410, a screw head 420, and an extension portion 430. The pedicle screw 410 (FIG. 12) has an upper end 412, a lower end 414, and a cannulated core 416 that extends between the ends 412, 414 and allows the screw 410 to be inserted over (and guided by) the K-wire 193. The upper end 412 is configured to be driven by the screwdriver 500, and may take a variety of shapes (e.g., hexagonal cavity 413, an octagonal cavity, etc.).

Figure 37:
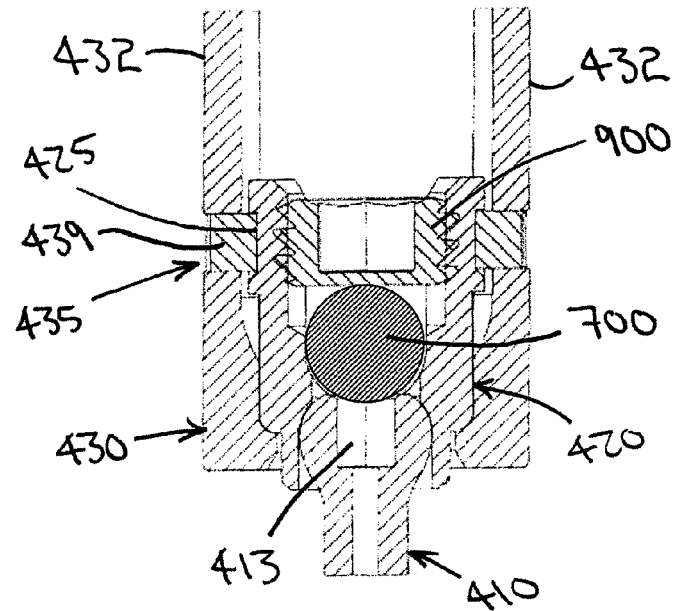
FIG. 37 is a sectional view showing the screw assembly of FIG. 10 in use with the rod of FIG. 35 and the cap of FIG. 36.

The screw head 420 (which may also be referred to herein as a "polyaxial head") is specifically shown in FIGS. 13 and 14 and is permanently fixed to the upper end 412 of the screw 410 through a ball-and-socket joint (see FIGS. 15, 16, and 37, though the structure that prevents the screw 410 from separating from the screw head 420 is not shown in the drawings). The ball-and-socket joint allows 360 degree rotation along the axis of the screw 410 and additionally allows the screw head 420 to pivot relative to the screw 410. The screw head 420 defines a receiving area 421 and may include structure 424 for coupling the screw head 420 to the extension portion 430.

The extension portion 430 is attached to the screw head 420 and includes at least two arms 432 to allow percutaenous placement of the screw 410 over the K-wire 193 and to allow percutaneous manipulation of the polyaxial head 420 while inserting a rod 700 and a cap screw 900, which are discussed below. An important development over the prior art concerns the extension portion 430 and the manner in which the extension portion 430 is coupled to the pedicle screw 410. As detailed in FIG. 18, the extension portion 430 may have at least one point of weakness or "defect" 433, allowing the extension portion 430 to be broken apart and separated from the head 420 when no longer needed. As best shown in FIG. 37, a catch 439 may interact with a cavity 425 in the head 420 (also shown in FIGS. 13 and 14) and a passage 435 (also shown in FIG. 17) in the extension portion 430 to temporarily couple the extension portion 430 to the screw head 420 (i.e., before the extension portion 430 is broken at the defect 433). While other means for fastening the screw head 420 to the extension portion 430 may also be used (e.g., a protrusion extending from the head 420 or the extension portion 430 interacting with a cavity in the extension portion 430 or the head 420, etc.), the catch 439 may allow the screw head 420 to be coupled to the extension portion 430 without further weakening the defect 433.

Attention is now directed to the screwdriver 500, shown in FIGS. 19a through 19c. The screwdriver 500 includes a shaft 510 having an end 512 complementary to the upper end 412 of the screw 410 for driving the screw 410, and the shaft 510 is hollow to allow the K-wire 193 to pass therethrough. In addition, a guide 520 is fixedly coupled to the shaft 510 (e.g., through welding, a set screw, or any other appropriate method/device) such that the guide 520 and shaft 510 rotate together. The guide 520 has passageways 522 configured to allow the arms 432 to pass through, temporarily securing the screwdriver 500 to the screw assembly 400. By securing the screwdriver 500 to the screw assembly 400 (i.e., to the arms 432), the screwdriver/percutaneous pedicle screw complex is more rigid, which may be desirable. To increase rigidity and prevent migration of the guide 520 along the arms 432, a set screw, complementary latching structure, and/or other fastening devices may be included to temporarily lock the guide 520 to the screw assembly 400. Though not shown, a handle may be coupled to the shaft 510 above the guide 520.

Figure 20:
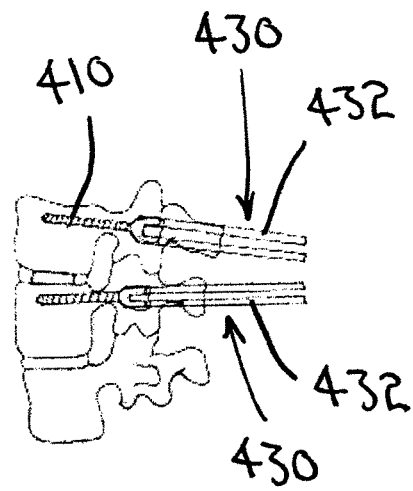
FIG. 20 illustrates placement of two screw assemblies of FIG. 10 within pedicles of adjacent vertebrae.
Figure 21:
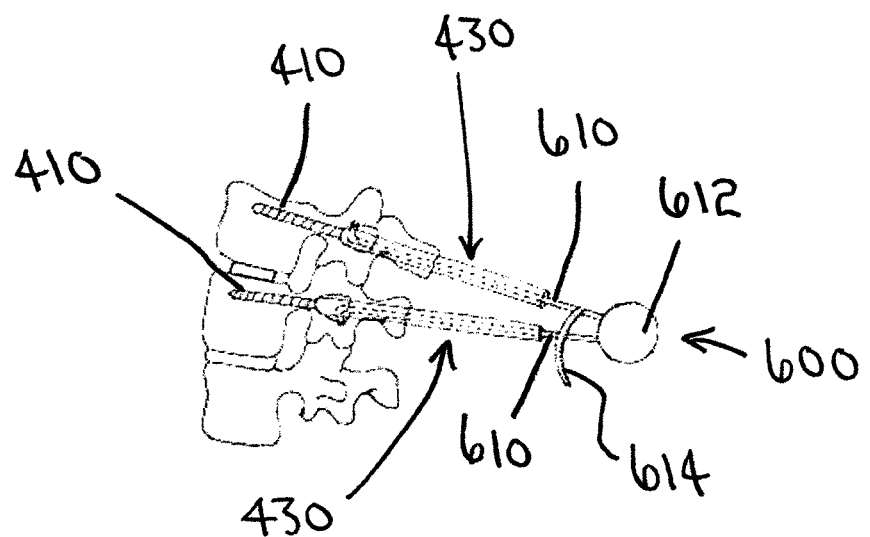
FIG. 21 illustrates a measurement device in use with the two screw assemblies of FIG. 20.

Once the screws 410 are in place in the pedicles 104 (or the pedicles 106), the screwdriver 500 and the K-wires 193 may be removed (FIG. 20). At this point in the procedure, the only devices extending through the patient's skin may be the extension arms 432 for each screw assembly 400. Because of their attachment to the screw heads 420, movement of the extension arms 432 may rotate the screw heads 420 three hundred and sixty degrees and also tilt the screw heads 420.

The desired rod 700 length is then selected. The rod length may be selected in various ways, such as by inspecting intraoperative fluoroscopic images or using a measurement device 600 (FIG. 21), for example. The measurement device 600 has two arms 610 operatively coupled together (e.g., by a pivot 612, a sliding mechanism, etc.), and a calibrated scale 614 is attached to one arm 610 such that the other arm 610 lines up with markings along the scale 614. The arms 610 of the measurement device 600 are passed through the skin of the patient along the extension portions 430 such that each arm 610 contacts one of the heads 420 of the two screw assemblies 400. A desired rod length is determined using the calibrated scale 614, and the appropriate length rod 700 is selected. The rod 700 is typically curved to allow reconstruction of the normal curvature of the lumbar spine; this curvature is known as lordosis. However, in some cases, the surgeon may select a straight rod 700. The scale 614 may add a predetermined distance (e.g., 10 mm) to the measured distance, and the ends of the arms 610 may be configured like ends of the rod 700; for example, each arm end may extend 5 mm (or another appropriate distance) outward from a respective screw head 420.

Figure 22:
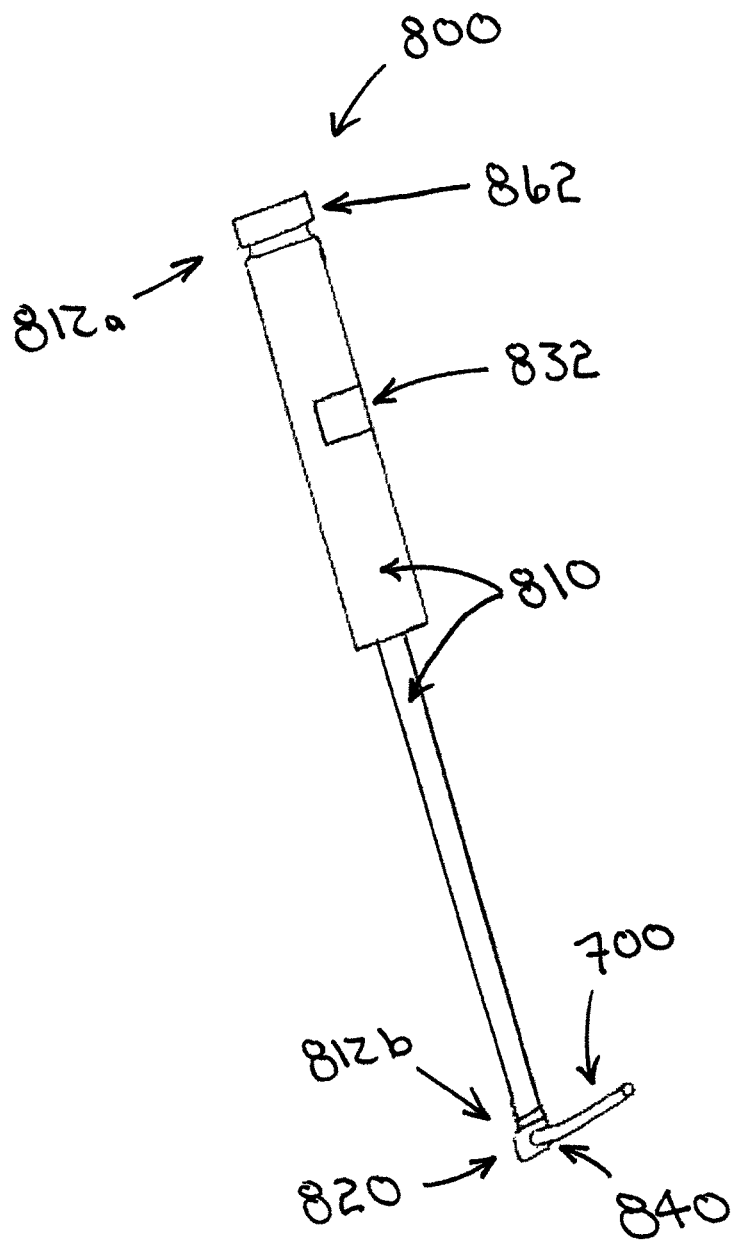
FIG. 22 is a perspective view of a rod insertion tool, according to an embodiment.

After the appropriate length rod 700 is selected, it is positioned using a percutaneous rod insertion tool 800 such that it is received in the receiving area 421 of the two screw heads 420. The rod insertion tool 800 is shown in detail in FIGS. 22 through 33. FIG. 22 shows the rod insertion tool 800 secured to the rod 700. As shown, the rod insertion tool 800 includes an elongate housing 810 having upper and lower ends 812a, 812b. The lower end 812b is shown having a smaller diameter than the upper end 812a; this allows the lower end 812b to function inside the patient's body as needed, and also allows the surgeon to easily maneuver the upper end 812a. The rod insertion tool 800 also includes a rotating end 820, a control system for the rotating end 820, an attachment device 840, and a control system for the attachment device 840.

Figure 23:
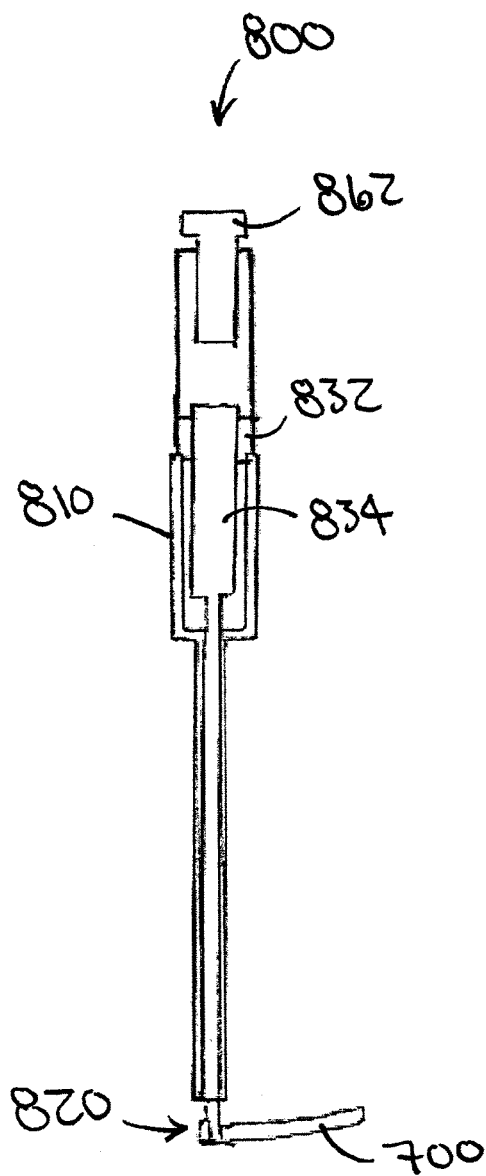
FIG. 23 is a sectional view of the rod insertion tool of FIG. 22.
Figure 24:
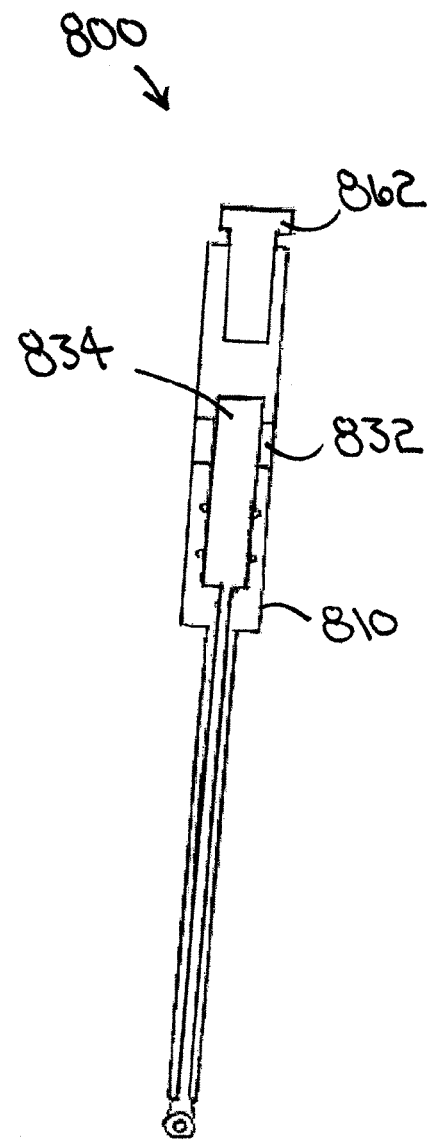
FIG. 24 is another sectional view of the rod insertion tool of FIG. 22.
Figure 25:
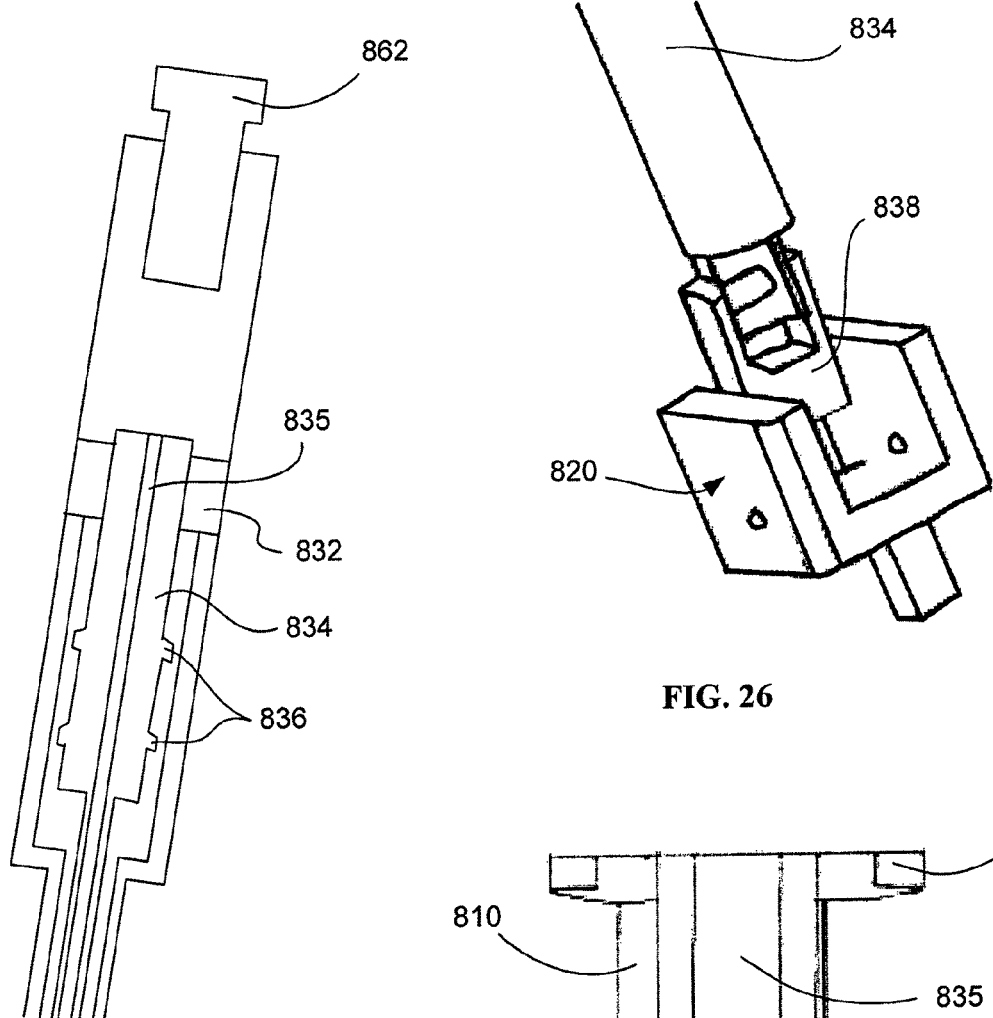
FIG. 25 is a detailed sectional view of the rod insertion tool of FIG. 22.
Figure 26:
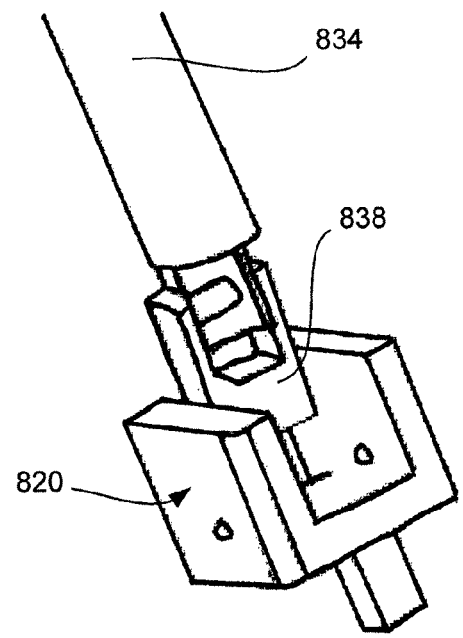
FIG. 26 is a partial view of the rod insertion tool of FIG. 22.
Figure 27:
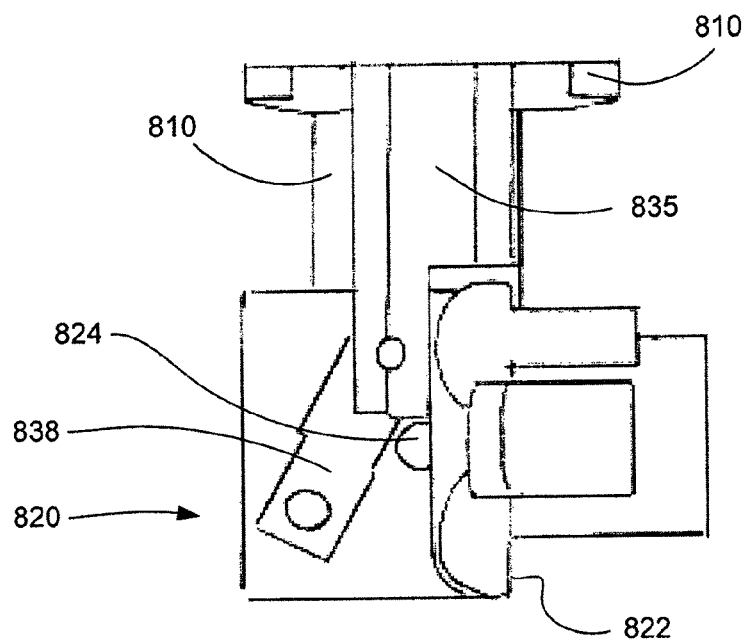
FIG. 27 is another detailed sectional view of the rod insertion tool of FIG. 22.

The rotating end 820 and the control system for the rotating end 820 are shown in FIGS. 23 through 27. The rotating end 820 is shown in detail in FIG. 27 and includes an attachment side 822 which rotates from a first position facing generally the same direction as the central axis of the housing 810 (FIG. 26) to a second position facing generally perpendicular to a central axis of the housing 810 (FIG. 27). When the rod 700 is coupled to the attachment device 840, the rod 700 extends generally parallel to the housing axis when the rotating end 820 is at the first position, and extends generally perpendicular to the housing axis when the rotating end 820 is at the second position (FIGS. 22 through 24). The rotating end 820 is pivotably coupled to the housing 810 at pivot point 824.

The control system for the rotating end 820 includes a thumbwheel 832 (FIGS. 22 through 25) and an internal plunger 834 (FIGS. 23 through 26). The thumbwheel 832 and the internal plunger 834 are configured with complementary structure such that rotation of the thumbwheel 832 causes the internal plunger 834 to become higher or lower relative to the housing 810. While various structures may be acceptably used to achieve this motion, one example is complementary threads, such that the thumbwheel 832 acts as a stationary nut and the plunger 834 acts as a linearly-moving screw. In such a configuration, only a portion of the plunger 834 needs to be threaded (i.e., the portion interacting with the thumbwheel 832 as the attachment side 822 moves between the first and second positions). To keep the plunger 834 from rotating (instead of moving linearly), the plunger 834 may interact with the housing 810 away from the threaded portion. For example, protrusions 836 (FIG. 25) on the plunger 834 may interact with rails or slots (not shown) in the housing 810. As shown in the drawings, the plunger 834 may include an internal channel 835.

To translate the linear movement of the plunger 834 into rotational movement of the rotating end 820, a link 838 may be pivotably coupled to the plunger 834 and the rotating end 820, as shown in FIGS. 26 and 27. When the plunger 834 is raised, the attachment side 822 may rotate about the pivot point 824 to the first position (FIG. 26), and when the plunger 834 is lowered, the attachment side 822 may rotate about the pivot point 824 to the second position (FIG. 27).

Figure 28:
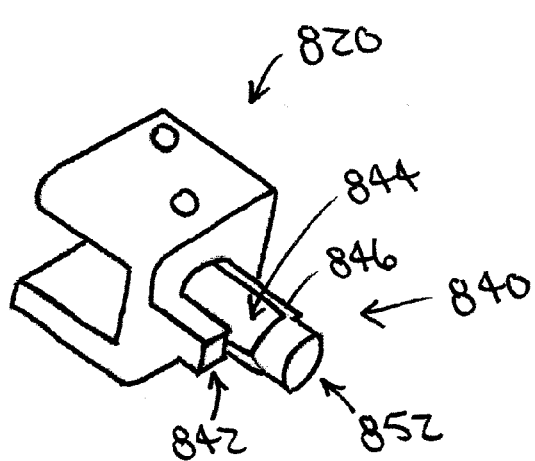
FIG. 28 is a perspective view of a rotating end and an attachment device from the rod insertion tool of FIG. 22.
Figure 29:
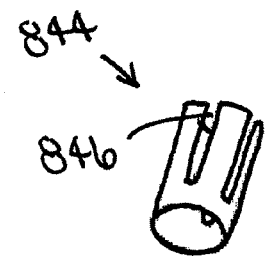
FIG. 29 is a perspective view of a deformable crown of the attachment device of FIG. 28.
Figure 30:
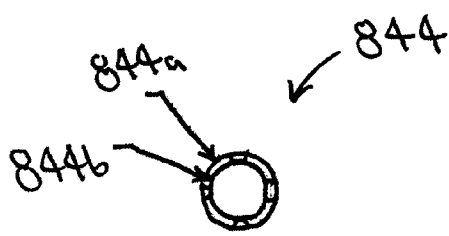
FIG. 30 is an end view of the deformable crown of FIG. 29.
Figure 31:
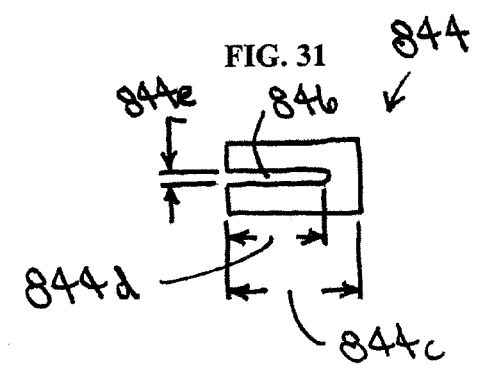
FIG. 31 is a side view of the deformable crown of FIG. 29.
Figure 32:
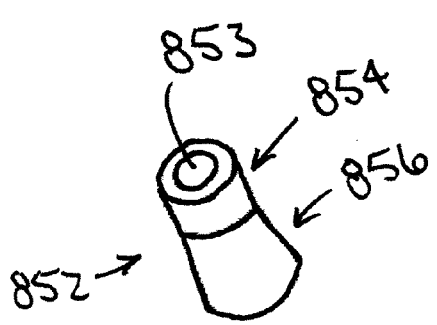
FIG. 32 is a perspective view of an actuator of the attachment device of FIG. 28.
Figure 33:
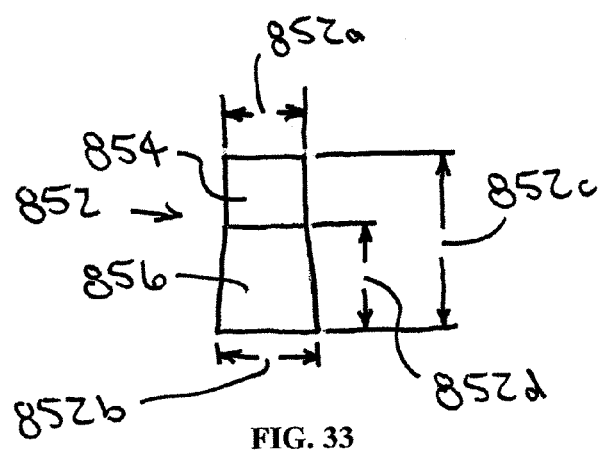
FIG. 33 is a side view of the actuator of FIG. 32.
Figure 34:
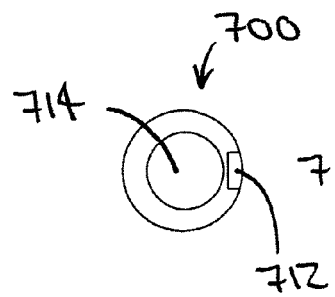
FIG. 34 is an end view of a rod, according to an embodiment.
Figure 35:
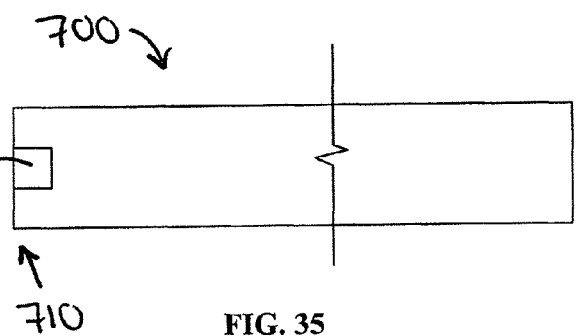
FIG. 35 is a side view of the rod of FIG. 34.

Turning now to the attachment device 840 and the control system for the attachment device 840, attention is directed specifically to FIGS. 22 and 28 through 33. The attachment device 840 includes a protrusion 842 (FIG. 28) for aligning the rod 700, a deformable crown 844 (FIGS. 28 through 31), and an actuator 852 (FIGS. 28, 32, and 33). The deformable crown 844 is naturally at a cylindrical configuration, as shown in FIGS. 28 through 31, and includes a plurality of expansion channels 846. While various materials and configurations may of course be acceptable, an exemplary crown 844 is constructed of a resilient material such as titanium, has an outer diameter 844*a* of approximately 0.12 inches, an inner diameter 844*b* of approximately 0.10 inches, a height 844*c* of approximately 0.216 inches, a channel depth 844*d* of approximately 0.16 inches, and a channel width 844*e* of approximately 0.02 inches.

The actuator 852 (FIGS. 28, 32, and 33) has a first portion 854 that is generally cylindrical and a second portion 856 that is generally conical, and the actuator 852 sits inside the crown 844 (FIG. 28). The actuator 852 may be configured such that the cylindrical portion 854 does not deform the crown 844, and the conical portion 856 causes the crown 844 to expand. While various materials and configurations may of course be acceptable, an exemplary actuator 852 is constructed of the same material as the crown 844, has an outer diameter 852*a* for the cylindrical portion 854 of approximately 0.09 inches, has a maximum diameter 852*b* for the conical portion 856 of approximately 0.11 inches, has an overall length 852*c* of approximately 0.2 inches, and has a length 852*d* for the conical portion 856 of approximately 0.12 inches.

The control system for the attachment device 840 includes a screw 862 (FIG. 22) and an internal cable (not shown). The internal cable extends from the screw 862 (which alternately may be a thumbwheel similar to thumbwheel 832, or may be any other device for causing linear movement of the internal cable) to the actuator 852 (e.g., to cavity 853) and passes through the internal channel 835 of the plunger 834. When the screw 862 is utilized to increase tension on the internal cable, the internal cable pulls the actuator 852 inward, causing the crown 844 to expand; when the screw 862 is utilized to reduce tension (or impart a pushing force upon) the internal cable, the internal cable pushes (or allows the actuator 852 to move) outward, allowing the crown 844 to contract (FIG. 28). The internal cable may be any appropriate structure capable of providing sufficient pulling and pushing forces, as described above and understood by one of skill in the art. An exemplary internal cable is constructed of 7×49 stainless steel with an outer diameter of approximately 0.044 inches.

In use, then, the rod 700 is selected, and is aligned such that the protrusion 842 mates with cavity 712 at one end 710 of the rod 700 (FIGS. 34 and 35), and the crown 844 and actuator 852 are inserted in cavity 714 of the rod 700 (FIG. 34) such that the crown 844 is generally cylindrical. The screw 862 is then used to increase tension on the internal cable, causing the actuator conical portion 856 to deform the crown 844. With the crown 844 deformed, the crown 844 exerts force on the rod 700, in effect locking the rod 700 to the attachment device 840.

Using the rod insertion tool 800, the rod 700 is inserted through the patient's skin (i.e., inside an extension portion 430) such that the rod 700 is generally aligned with the center axis of the shell 820. Once the rod 700 is inserted, the thumbwheel 832 is rotated, causing the internal plunger 834 to lower and the rotating end 820 (and the attached rod 700) to rotate. After the rod 700 is received in the receiving areas 421 of the two screw heads 420, the screw 862 is used to provide a pushing force (or release tension) on the internal cable, allowing the actuator conical portion 856 to exit the crown 844 and the crown 844 to return to the cylindrical configuration. With the crown 844 at the cylindrical configuration, the attachment device 840 may be separated from the rod 700 and the rod insertion tool 800 may be removed.

Figure 36:
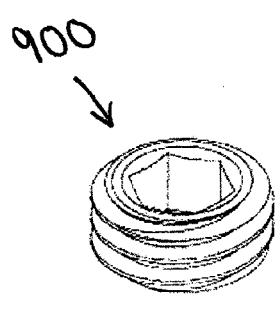
FIG. 36 is a perspective view of a cap, according to an embodiment.
Figure 38:
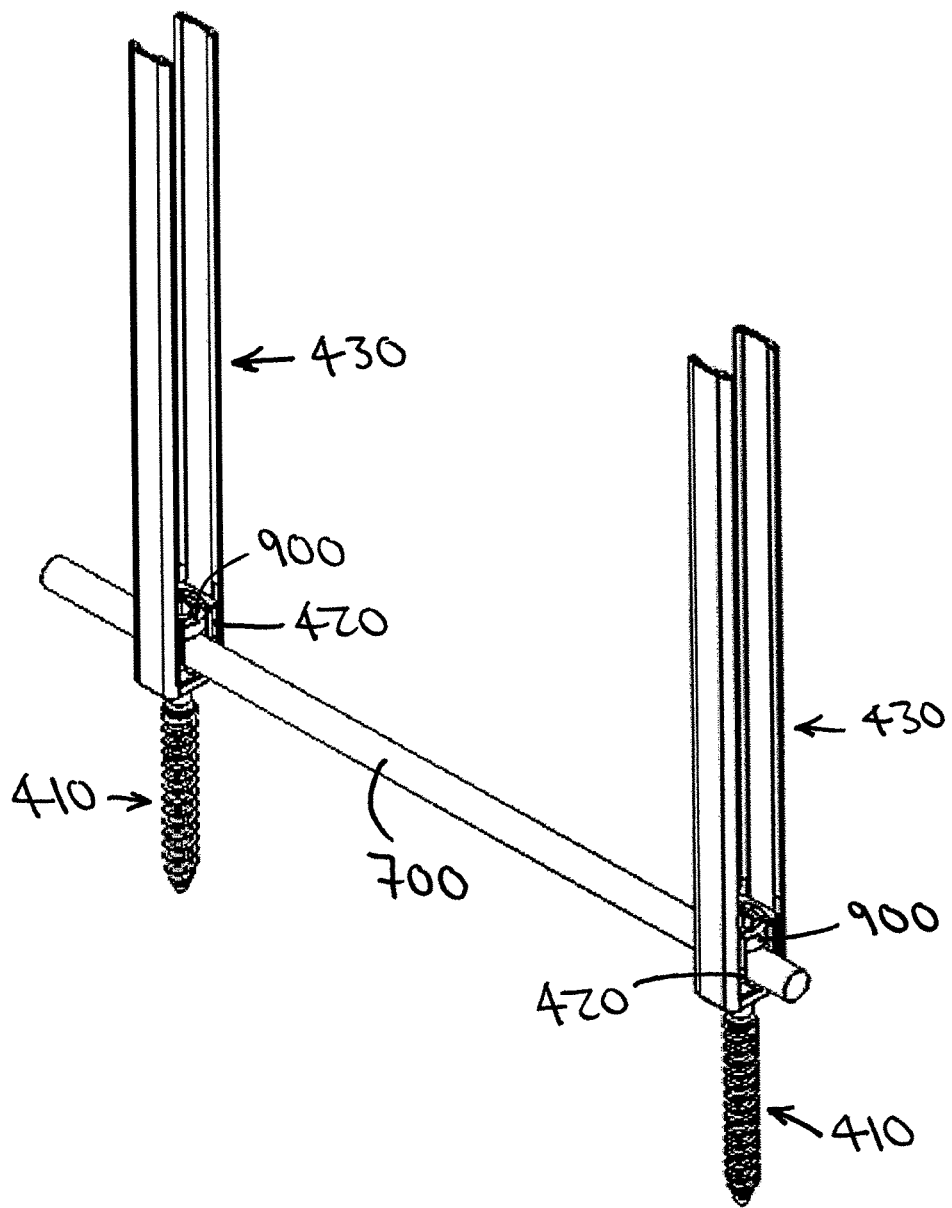
FIG. 38 is a perspective view showing two screw assemblies of FIG. 10 in use with the rod of FIG. 35 and two caps of FIG. 36.

Turning to FIGS. 36 through 38, once the rod 700 is in place in the receiving areas 421 of the two screw heads 420, a cap 900 is fixed to a threaded portion of each of the screw heads 420. The caps 900 may be placed using the screwdriver 500 or another tool (e.g., a simple screwdriver having an appropriate driving mechanism), and the caps 900 lock the rod 700 in place by exerting force on the rod 700.

Figure 39:
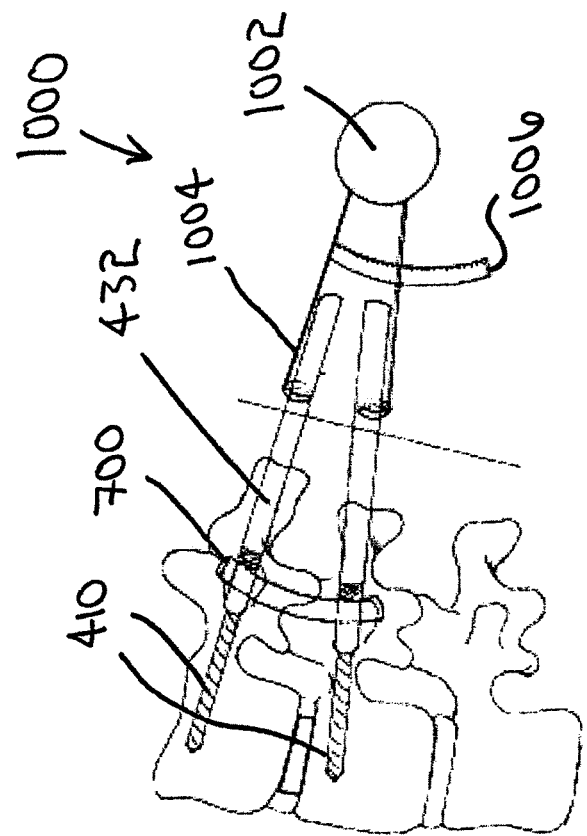
FIG. 39 illustrates a compressor device, according to an embodiment, in use with the two screw assemblies of FIG. 10.

If compression is desired, one of the caps 900 is set in place and tightened, and the other cap 900 is set in place but not yet tightened. Before the second cap 900 is tightened, a compressor device 1000 is fitted onto the arms 432 of each extension portion 430 (FIG. 39). Pressure is then applied from the compressor device 1000 to the arms 432 to provide compressive stress across the instrumentation construct to improve interbody fusion device surface area contact with the adjacent vertebral body endplates, thus increasing the probability of successful fusion of the vertebrae during healing and minimizing post-operative interbody graft migration. While compressive forces are applied, the second cap 900 is tightened, securing the rod 700 in a compressed position. The extension portions 430 of adjacent screw assemblies 400 may overlap slightly during compression; this is possible because the extension portions 430 of adjacent screw assemblies 400 are thin and low profile, which allows more effective compression.

Figure 40:
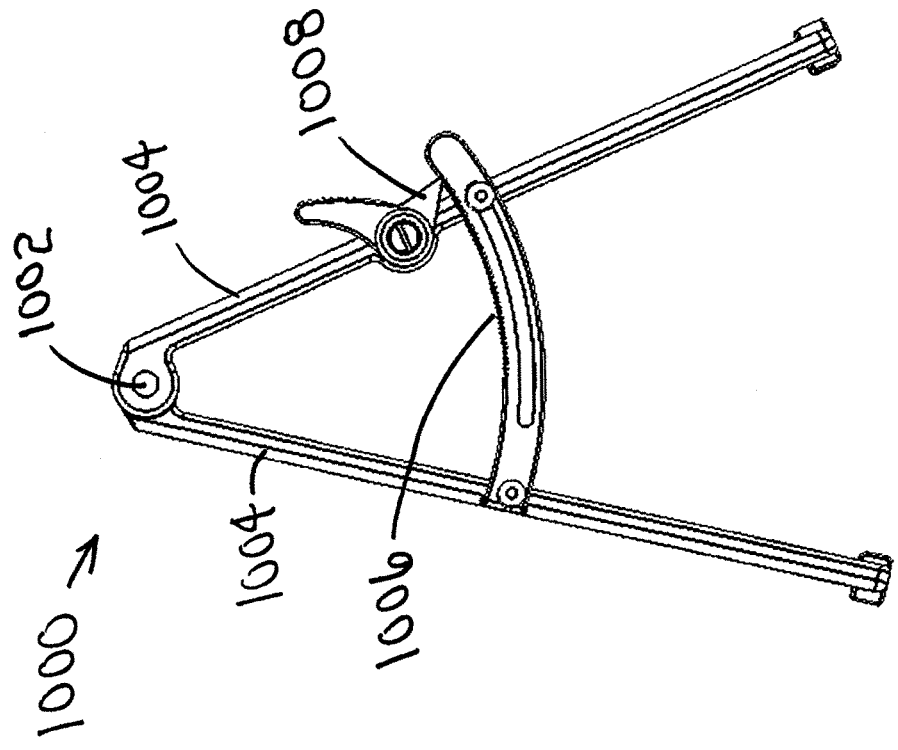
FIG. 40 is a front view of the compressor device of FIG. 39.
Figure 42:
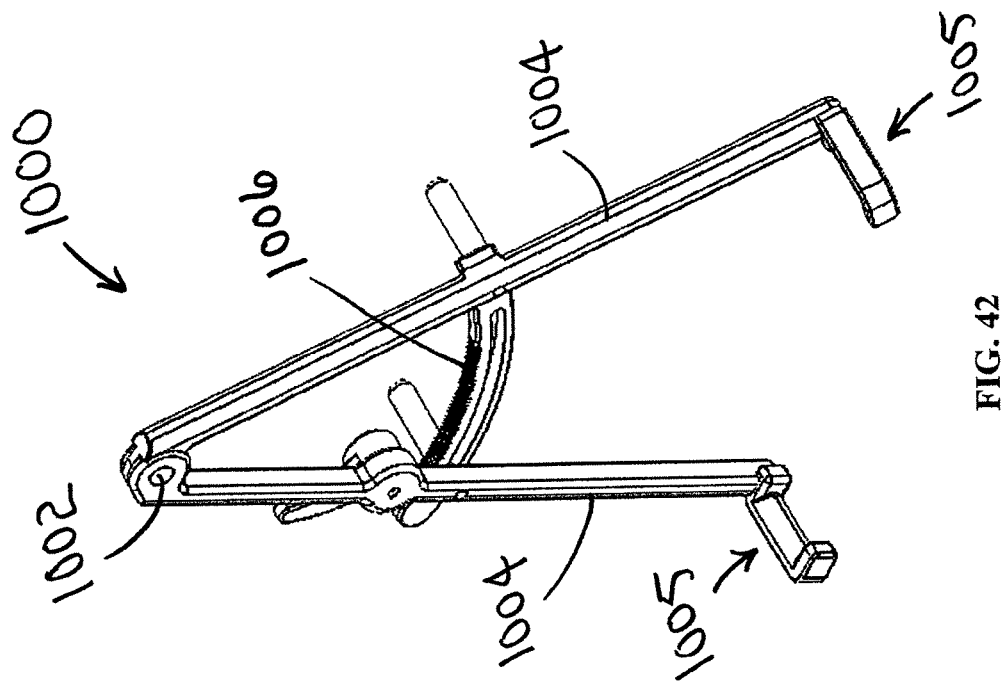
FIG. 42 is another perspective view of the compressor device of FIG. 40.
Figure 41:
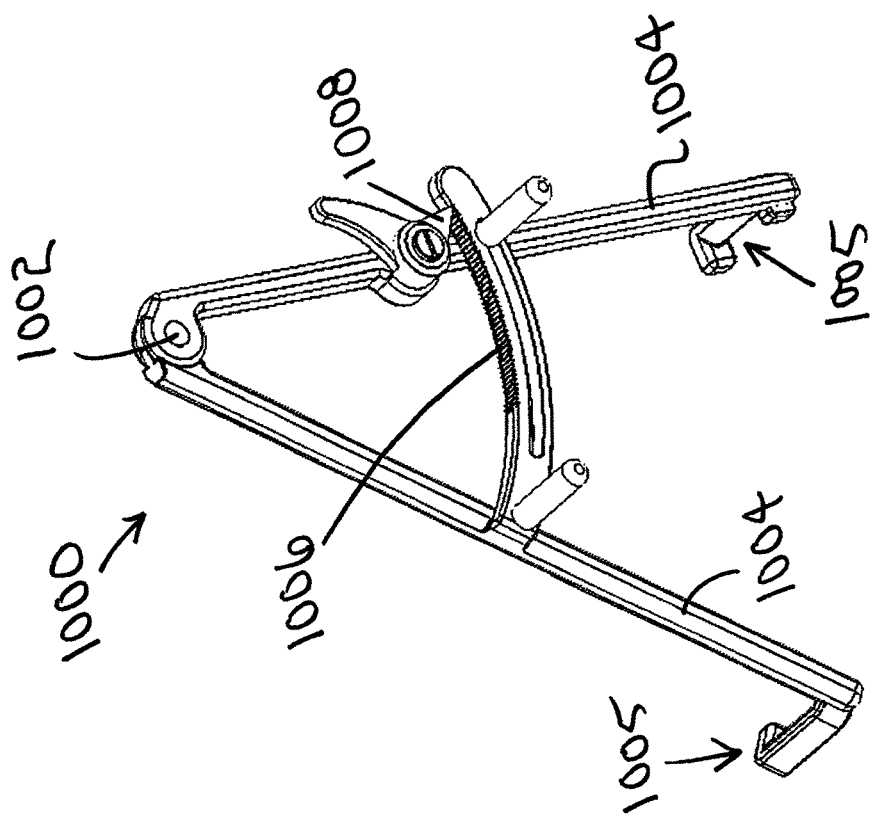
FIG. 41 is a perspective view of the compressor device of FIG. 40.

The compressor device 1000 is shown in detail in FIGS. 40 through 42 and has a pivot 1002, two arms 1004, and a notched indicator 1006 attached to one arm 1004. Each arm 1004 has an attachment portion 1005 (FIGS. 41 and 42) configured for attachment to the extension portions 430 of the screw assemblies 400. A tooth 1008 coupled to the second arm 1004 can be advanced along the notched indicator 1006 in the manner of a ratchet to set and maintain a desired level of compression. More particularly, the notched indicator 1006 has a toothed side that engages the tooth 1008 on the second arm 1004 to maintain a compressed state. Compression is maintained until the tooth 1008 is released from the indicator 1006 to permit removal of the compressor device 1000 from the extension portions 430 after the second cap 900 is tightened.

Figures 17, 18:
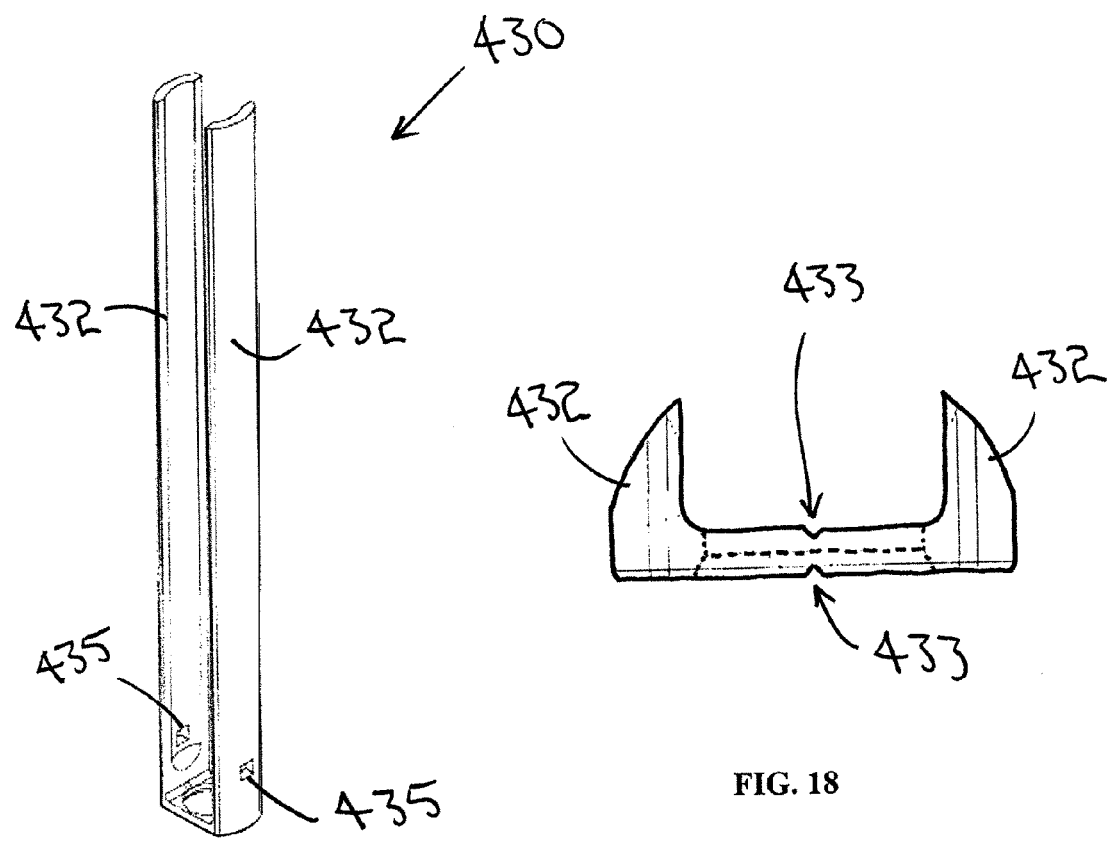
FIG. 17 is a perspective view of the extension portion from the screw assembly of FIG. 10.
FIG. 18 is a partial view of the extension portion of FIG. 17.

After the rod 700 is in place and both caps 900 are tightened, the extension portions 430 may be removed from the pedicle screws 410 and the screw heads 420 by simply pulling the arms 432 away from one another, causing the extension portions 430 to fail at the defects 433, which are best shown in FIG. 18. In an exemplary embodiment, approximately a 30° angle between the arms 432 is required to separate the extension portions 430 from the pedicle screws 410 and the screw heads 420; this of course can be altered (e.g., by altering the design of the defects 433), however. Once the extension portions 430 are removed, the fascia and skin may be closed, and the procedure may be concluded.

In prior art percutaneous pedicle screw systems, early release of the percutaneous screw extensions is a significant problem. This typically requires complete removal of the pedicle screw, and a larger diameter pedicle screw/extension complex is then assembled and re-inserted into the pedicle over a new K-wire. This requires extensive operative time, and can be a major source of patient morbidity. Salvage tool 1500 (shown in FIGS. 43a through 46) effectively reconstructs the extension portion 430 in the event that the extension portion 430 is released prematurely; this avoids the need for pedicle screw removal and replacement. To be clear, salvage tool 1500 is currently not intended to be used in every surgery, or even routinely, but is instead a device which may be used if necessary.

Figure 43A:
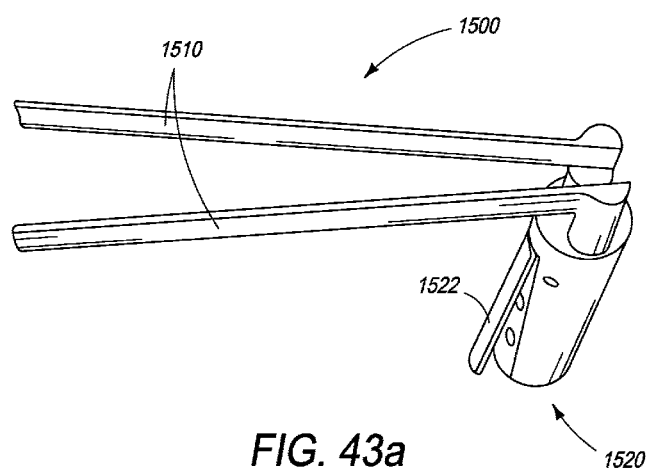
FIG. 43a is a perspective view of a salvage tool, according to an embodiment, with its extensions at an open alignment.
Figure 43B:
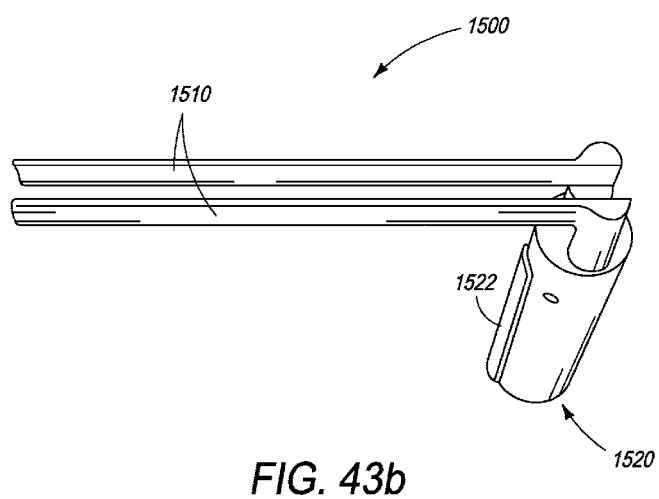
FIG. 43b is a perspective view of the salvage tool of FIG. 43a, with its extensions at a closed alignment.
Figures 45, 46:
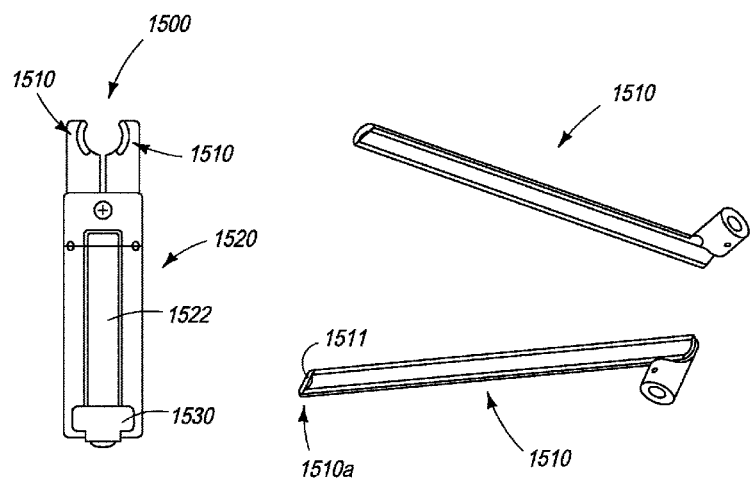
FIG. 45 is a front view of the salvage tool of FIG. 44.
FIG. 46 is a perspective view of the extensions of the salvage tool of FIG. 44.
Figure 47:
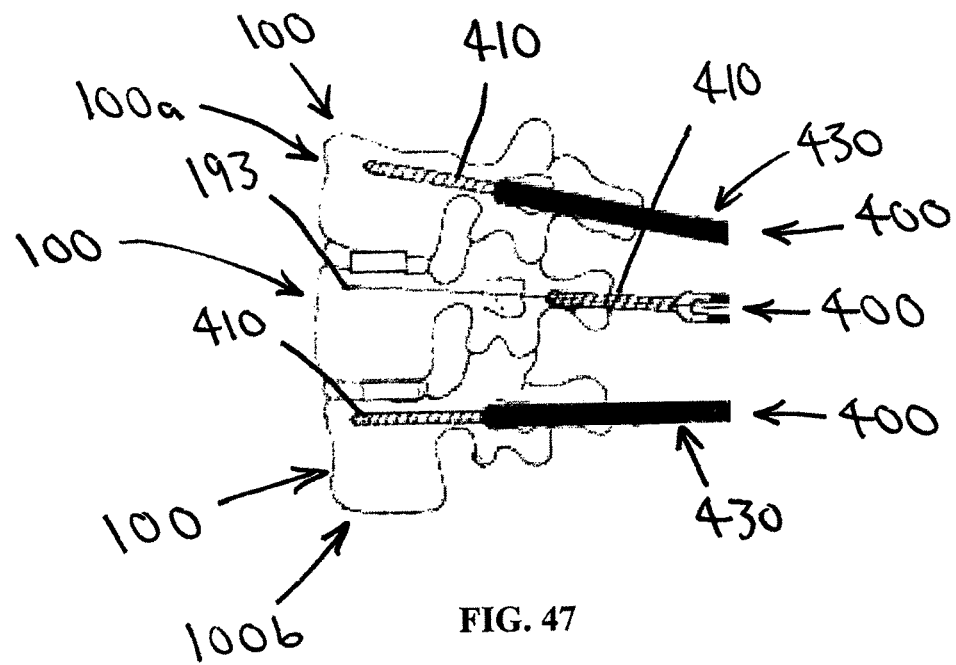
FIG. 47 illustrates placement of three screw assemblies of FIG. 10 for a two level procedure.

The salvage tool 1500 contains two extensions 1510 that are manufactured to the same dimensions and configurations as the original extension portion 430. Salvage tool 1500 also contains a trigger 1522 along a handle 1520. By pulling the trigger 1522, the two extension arms 1510 are brought from an open alignment (FIG. 43a) into a closed (parallel) alignment (FIGS. 43b and 45). This may be accomplished, for example, through linkage coupled to at least one of the extensions 1510 and operable by the trigger 1522 to rotate the extension 1510 to the closed alignment when the trigger 1522 is pressed. Various other mechanical systems may alternately be used to rotate at least one of the extensions 1510 upon pressing the trigger 1522, as will be clear to one skilled in the art.

Figure 44:
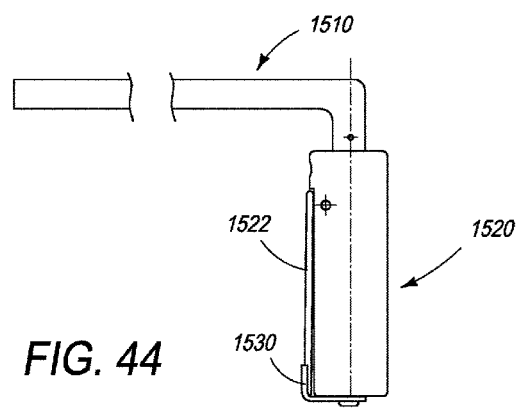
FIG. 44 is a side view of the salvage tool of FIG. 43b.

The extension(s) 1510 may be biased to the open alignment (e.g., by one or more spring), and a lock 1530 may be employed to maintain the extension(s) 1510 at the closed alignment for a period of time. The lock 1530 shown in FIGS. 44 and 45 is simply a catch that is rotatable about the handle 1520 to maintain the trigger 1522 at the pressed configuration until released. Again, various other mechanical devices may alternately be used to lock the extension(s) 1510 at the closed alignment, as will be clear to one skilled in the art.

To use the salvage tool 1500 (e.g., in the event of premature separation of extension portions 430 from pedicle screw 410), the extensions 1510 are inserted adjacent the screw head 420. The trigger 1522 is then pulled, bringing the extensions 1510 to the closed alignment along the screw head 420, and the lock 1530 may be employed. As shown in FIG. 46, a ledge (or "wall") 1511 may be located at the distal end 1510a of each extension 1510 to extend along the lower side of the screw head 420 when the extensions 1510 are in place. The extension portions 430 are thus reconstructed, allowing the operation to continue (e.g., the rod 700 may be positioned and/or secured) without having to convert to an open procedure or remove and replace the pedicle screw 410.

While the procedure set forth above includes only two screw assemblies 400, multilevel procedures may also be performed using the equipment and techniques set forth above. As an example, a two level minimally invasive procedure according to one embodiment is shown and described with reference to the above description and FIGS. 1 through 46 of the accompanying drawings, and additionally with reference to FIGS. 47 through 56 of the accompanying drawings.

For a two level procedure, the steps set forth above to fuse vertebrae 100 (i.e., the steps utilizing the port 200) are repeated on an additional adjacent vertebra 100 such that the additional vertebra 100 is similarly fused. This situation is shown schematically in FIG. 47.

For a multilevel fusion, screw assemblies 400 are first fixed to the upper and lower vertebrae 100a, 100b (FIG. 47) in the same manner as described above (i.e., starting with placement of Jamshidi needles and ending with removal of the screwdriver 500 and the K-wires 193 after the screws 410 are in place in the pedicles 104 or 106). Next, an alignment tool 1600 is attached to the extension portion 430 of the fixed screw assemblies 400.

The alignment tool 1600 is shown in FIGS. 48 through 56 and includes opposed rails 1610 (identified individually as 1610a and 1610b) and a plurality of receiving members 1620. In some embodiments, at least one of the receiving members 1620 is permanently coupled to at least one of the rails 1610 such that it may or may not be movable along the rail 1610 but cannot be separated from the rail 1610. In other embodiments, all of the receiving members 1620 are removably coupled to the rails 1610.

Figure 48:
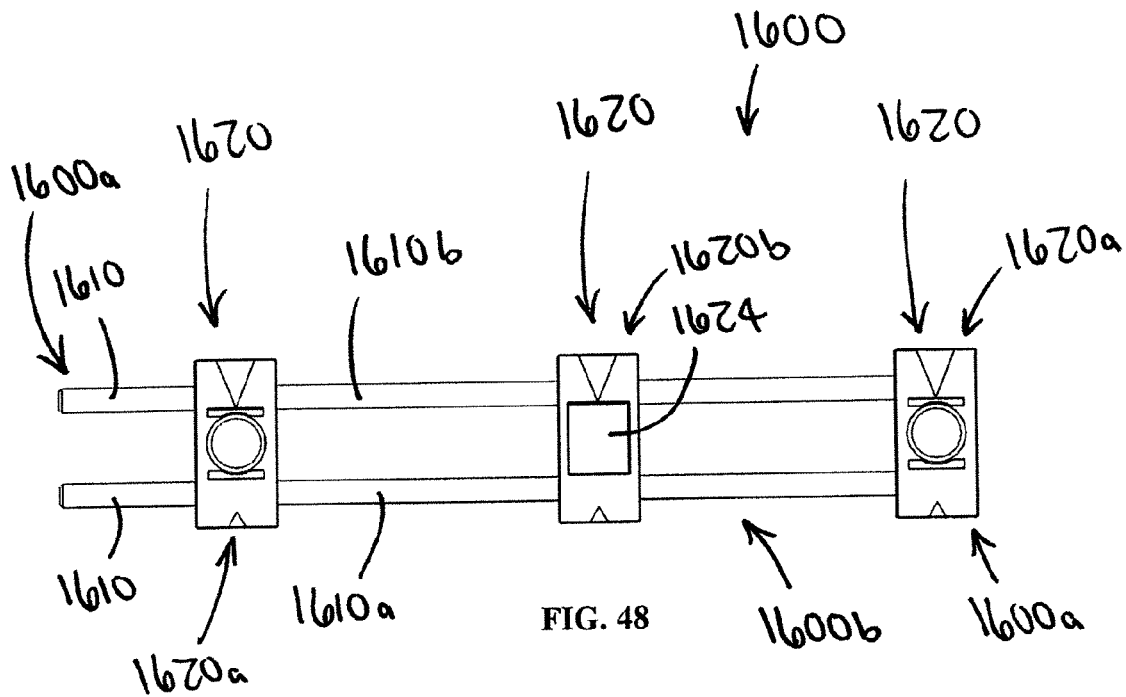
FIG. 48 is a top view of an alignment tool, according to an embodiment.
Figure 49:
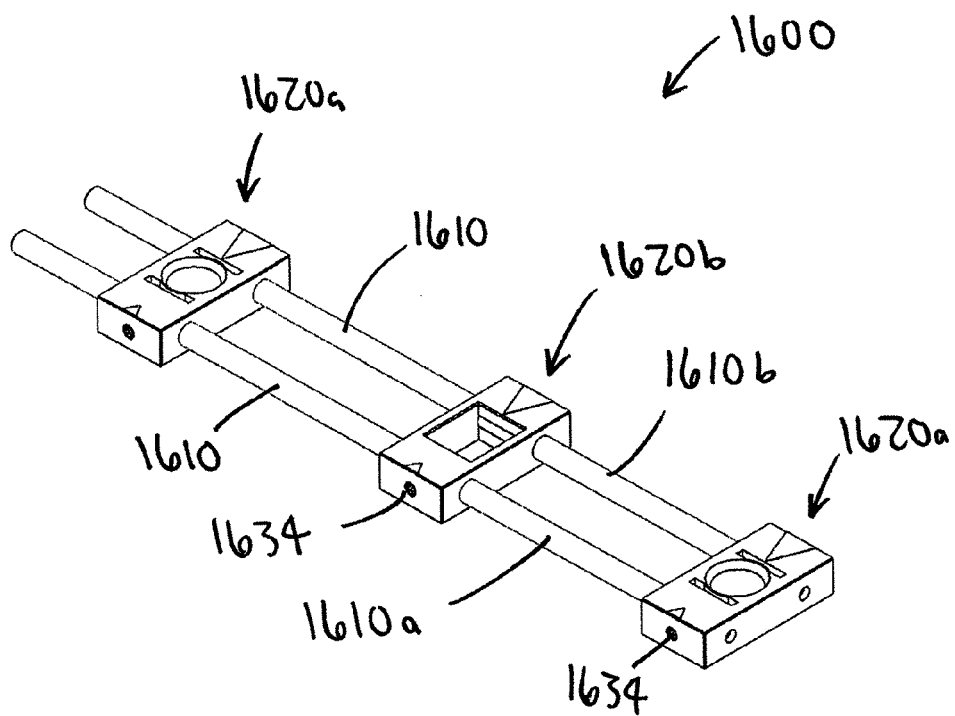
FIG. 49 is a perspective view of the alignment tool of FIG. 48.
Figure 53A:
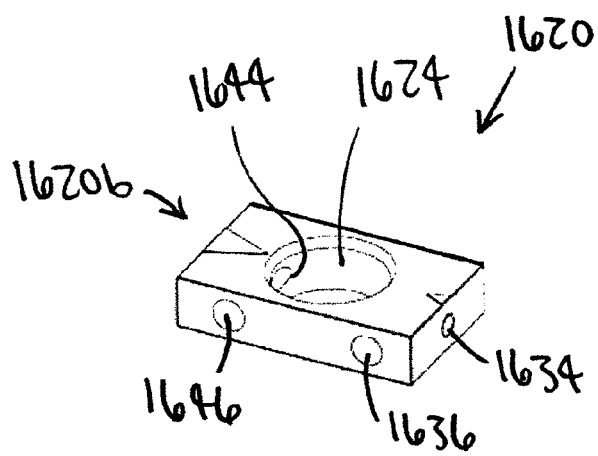
FIG. 53a is a perspective view of another receiving member of the alignment tool of FIG. 48.
Figure 53B:
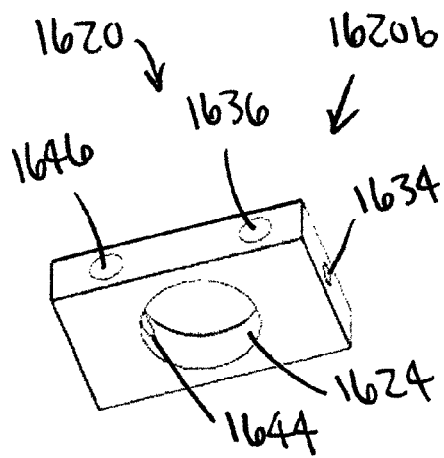
Figure 54:
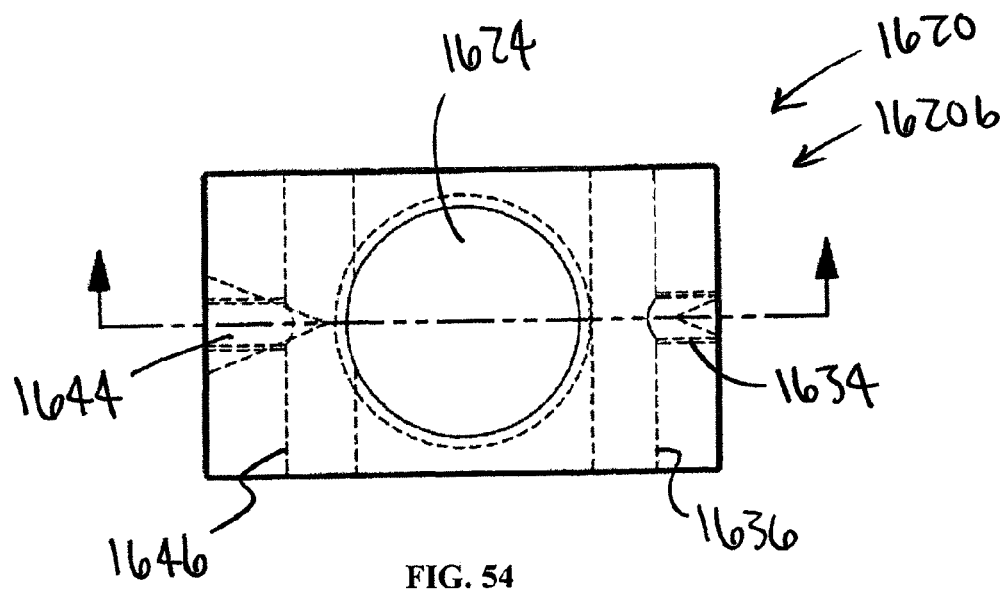
Figure 55:
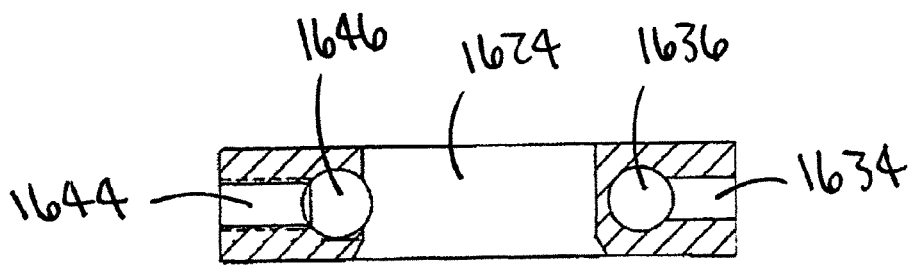

Each receiving member 1620 is configured to receive a respective extension portion 430. In some embodiments, as shown in FIGS. 48 through 56, the receiving members 1620 for use at the ends 1600a of the alignment tool 1600 each have first and second holes 1622a, 1622b configured to receive the arms 432 of respective extension portions 430 (these receiving members 1620 are identified individually as 1620a), while receiving members 1620 for use in a middle region 1600b of the alignment tool 1600 each have a single hole 1624 for receiving the arms 432 of respective extension portions 430 (these receiving members 1620 are identified individually as 1620b). The holes 1624 may be rectangular, as shown in FIGS. 48 and 49, or may be circular, as shown in FIGS. 53a through 56, or may be any other appropriate shape. A circular shape may be desirable for allowing easier rotation of the extension portion 430 inside the hole 1624. While only one receiving member 1620b is shown in the drawings, it should be appreciated that additional receiving members 1620b may be required for procedures requiring placement of four or more pedicle screws 410.

If a receiving member 1620 is movable along the rails 1610, a locking device is preferably included to restrict the receiving member 1620 from moving from a desired location along the rail 1610a. For example a set screw 1632 (FIGS. 50a and 50b) operable by the user may extend through hole 1634 in the receiving device 1620 to interact with the rail 1610a passing through hole 1636 in the receiving device 1620, effectively locking the receiving member 1620 to the rail 1610a. While a specific embodiment of a locking device is shown in the accompanying drawings, one skilled in the art will appreciate that other locking devices and configurations may alternately, or additionally, be used.

Additionally, a locking device is preferably included to restrict the receiving member 1620 from moving from a desired location along the arms 432 of a respective extension portion 430. For example, a set screw 1642 (FIGS. 50a and 50b) operable by the user may extend through hole 1644 in the receiving device 1620 to interact with the rail 1610b passing through hole 1646 in the receiving device 1620. Because pressure on the rail 1610*b* from set screw 1640 causes the rail 1610*b* to exert pressure on the arm 432 (which passes through hole 1622*b* for receiving members 1620*a*, and which passes through hole 1624 for receiving members 1620*b*), this effectively locks the receiving member 1620 to both the rail 1610*b* and the arm 432. While a specific embodiment of a locking device is shown in the accompanying drawings, one skilled in the art will appreciate that other locking devices and configurations may alternately, or additionally, be used.

In use, then, the extension portions 430 of the upper and lower screw assemblies 400 are coupled to respective receiving members 1620 (e.g., receiving members 1620*a*), which may require adjusting the receiving members 1620 along the rails 1610, as set forth above. Once in place, the locking devices are used to fix the receiving members 1620 to the rails 1610 and also to fix the receiving members 1620 to the extension portions 430. At this point, intraoperative fluoroscopy may be utilized. The unlocked receiving member 1620 (e.g., receiving member 1620*b*), and specifically the hole 1624, is aligned with the pedicle 106 (or the pedicle 108) and fixed to the rails 1610, as set forth above.

Figure 56:
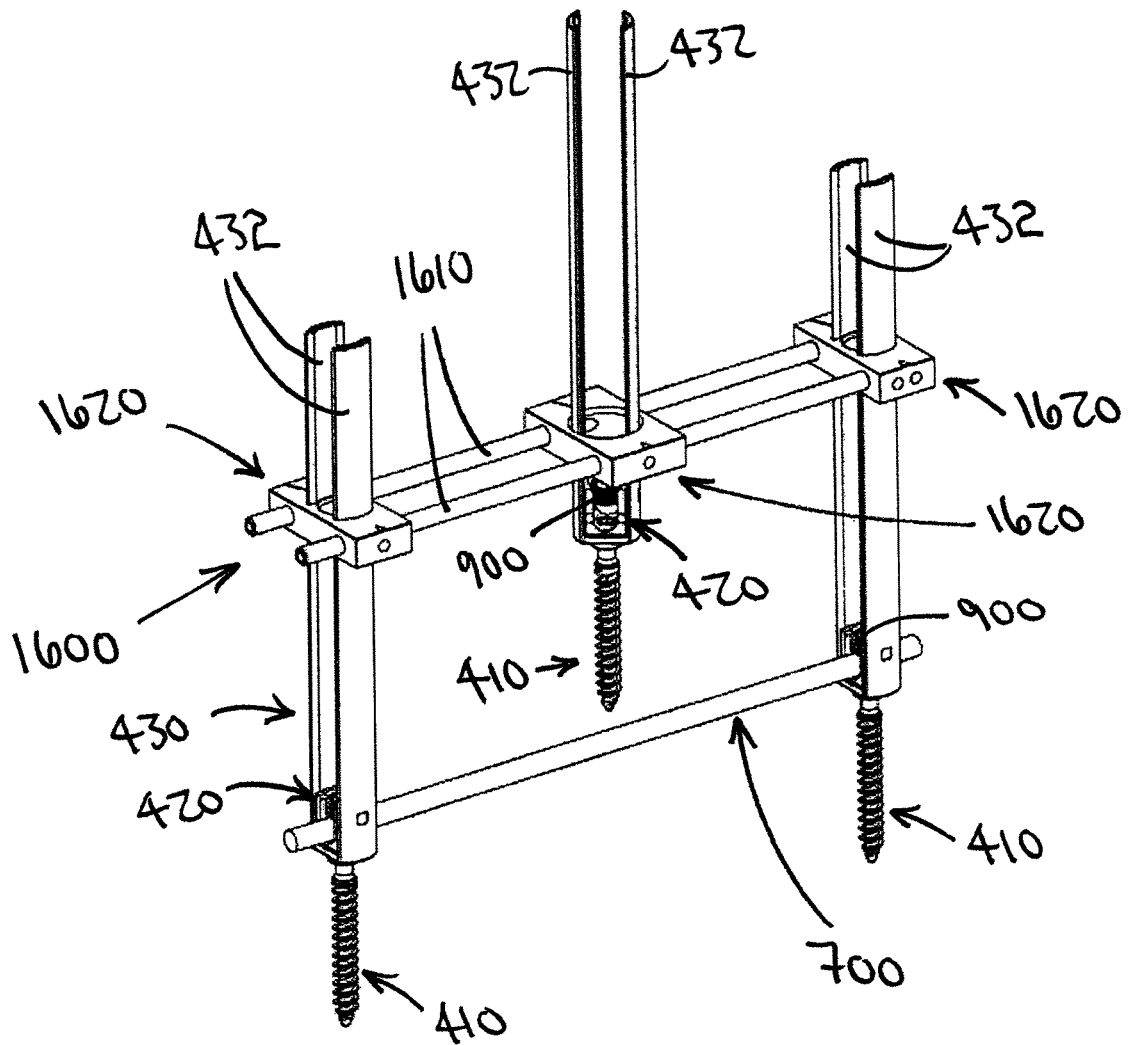
FIG. 56 is a perspective view of the three screw assemblies of FIG. 47, in use with the alignment tool of FIG. 48, the rod of FIG. 35, and caps of FIG. 36; it should be appreciated that the rod would never be placed as shown until after all of the screw assemblies are received in bone, and that the caps would not be set in place until after the rod is positioned in all three screw assemblies.

Next, the remaining screw assembly 400 is fixed to the remaining vertebra 100 in the same manner as described above and used for the prior two screw assemblies 400 (i.e., starting with placement of a Jamshidi needle and ending with removal of the screwdriver 500 and the K-wire 193 after the screw 410 is in place in the pedicle 104 or 106), though the Jamshidi needle, the K-wire 193, and the screw assembly 400 are all inserted through the hole 1624. By using the alignment tool 1600 (e.g., by working through the hole 1624), all of the screw heads 420 will be aligned to receive the rod 700. This is generally shown in FIG. 56, though it should be appreciated that the rod 700 would never be in place before all of the screw assemblies 400 are in place, and that the caps 900 would not be set in place until after the rod 700 is positioned in all three receiving areas 421.

The rod 700 is selected as set forth above. Next, using the rod insertion tool 800, the rod 700 is positioned through the extension portion 430 of the upper screw assembly 400 or the lower screw assembly 400, and rotated, as set forth above, such that the rod 700 is positioned in all three receiving areas 421 of the screw heads 420. Caps 900 are then set in place as described above, and only one cap 900 (e.g., the cap 900 in the middle) is tightened. Once the caps 900 are set in place, the alignment tool 1600 may be released from the extension portions 430 and set aside.

If compression is desired, the compressor device 1000 may be used generally as set forth above. The upper or lower screw assembly 400 is first compressed with the central screw assembly 400 and locked into place by tightening the appropriate cap 900, and then the other screw assembly 400 is compressed with the central screw assembly 400 and locked into place by tightening the remaining cap 900. To conclude the procedure, the extension portions 430 may be removed from the pedicle screws 410 and the screw heads 420 as set forth above, and the fascia and skin may be closed.

Figure 57:
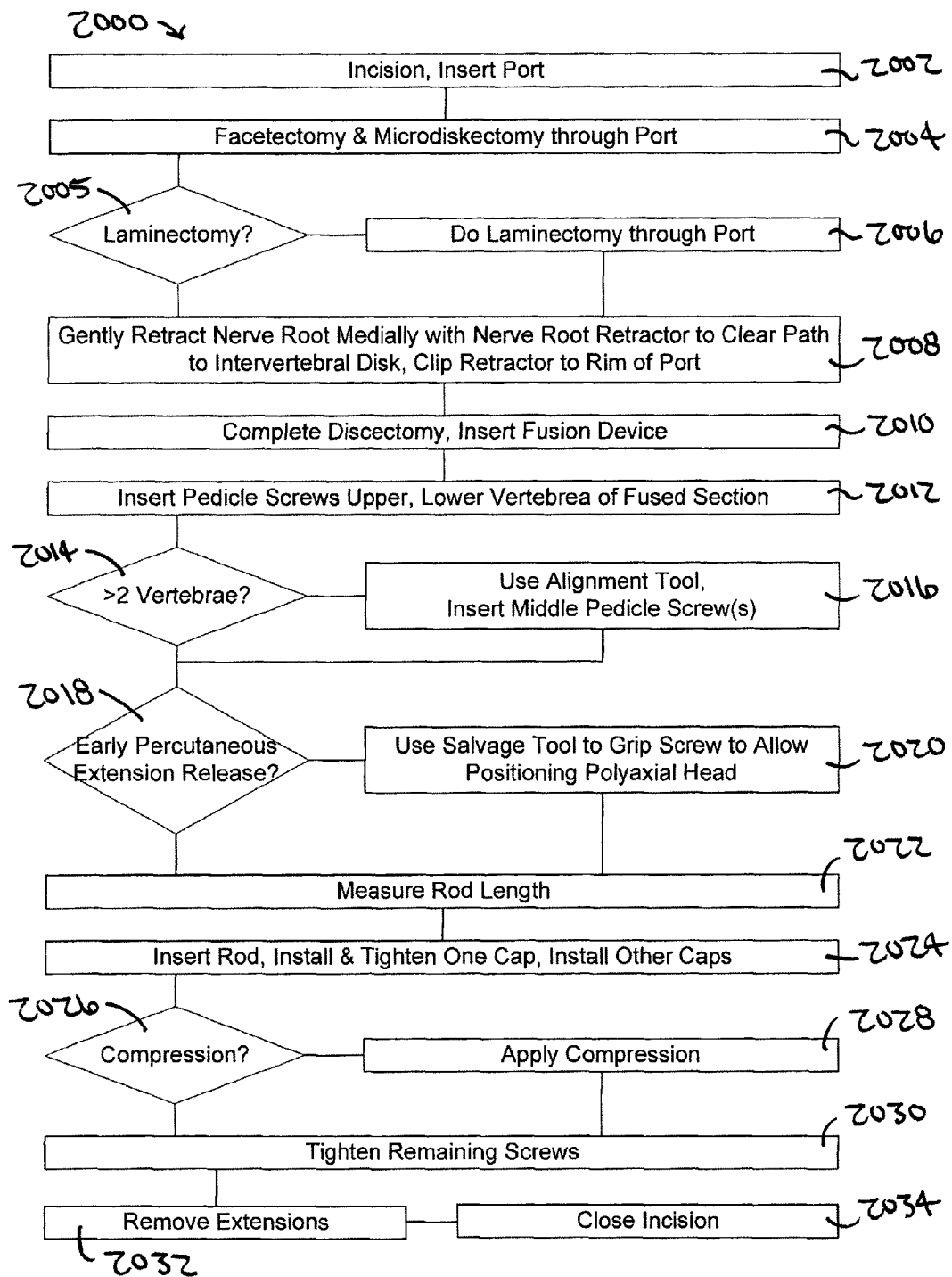
FIG. 57 is a flowchart summarizing various surgical procedures set forth herein.

A summary of the procedures described above is illustrated in the flowchart of FIG. 57. Procedure 2000 begins with an incision 2002 for a posterior approach to the patient's spine. The port 200 is then inserted through the skin incision until it is flush with the facet 118. The decompression is then performed at step 2004 through the port 200, which includes a facetectomy and microdiscectomy. If a laminectomy is needed (see step 2005), it is performed at step 2006 through the port 200, and then the procedure 2000 continues to step 2008; if a laminectomy is not needed, the procedure 2000 continues from step 2004 to step 2008.

At step 2008, the nerve root is gently retracted medially with a nerve root retractor 180 that may be attached to the port 200. The discectomy is then completed at step 2010, and the interbody fusion device 190 is inserted through the port 200 into the intervertebral space between the vertebral bodies 102 to elicit arthrodesis. The port 200 is then removed, and the procedure 2000 continues to step 2012.

At step 2012, K-wires 193 are inserted into the pedicles 104 (or 106) of the vertebrae using Jamshidi needles, and cannulated pedicle screws 410 (of screw assemblies 400) are inserted percutaneously over the K-wires 193 into the upper and lower vertebrae 100 of the spinal segment to be stabilized.

If a multilevel fusion is performed (see step 2014), the alignment tool 1600 is placed over the percutaneous extensions 430 of the screw assemblies 400 and then the intervening pedicle screw(s) 410 is/are inserted through the alignment tool 1600 at step 2016. This guarantees alignment of the middle pedicle screw(s) 410 within the construct, thereby facilitating rod placement, and the procedure 2000 continues to step 2018. If more than two vertebrae are not involved, the procedure 2000 moves from step 2012 to step 2018.

If an extension portion 430 of a screw assembly 400 is accidentally released prematurely (see step 2018), the salvage tool 1500 is used at step 2020 to grip the screw head 420, allowing completion of the procedure 2000 without replacing the pedicle screw assembly 400; the procedure 2000 then continues to step 2022. If the extension portion 430 is not released prematurely, the procedure 2000 moves from step 2018 to step 2022.

At step 2022, the appropriate rod length is measured (e.g., from intraoperative fluoroscopic images or using the measurement device 600), and the procedure 2000 continues to step 2024.

At step 2024, the rod 700 having the appropriate length is selected and inserted into the rod insertion tool 800. The rod insertion tool 800 is then used to insert the rod 700 between the percutaneous screw extensions 430 of the most caudad or cephalad pedicle screw assembly 400 within the construct. Next, the rod 700 is rotated into position within the receiving areas 421 of the polyaxial heads 420, and the caps 900 are set in place. One cap 900 is tightened, securing the rod 700 in place.

The procedure 2000 then moves to step 2026, where different paths are taken depending on whether compression is desired. If so, the procedure 2000 continues to step 2028; if not, the procedure 2000 continues to step 2030.

At step 2028, the compressor device 1000 is fitted onto the extension portions 430 and adjusted to provide the amount of compression that is desired. The untightened caps 900 are tightened while compression is applied to maintain the instrumentation construct in the compressed position, and the compressor device 1000 is set aside. The procedure 2000 then moves to step 2032.

At step 2030, the untightened caps 900 are fully tightened to finish securing the rod 700 in place, and the procedure 2000 continues to step 2032.

At step 2032, the extension portions 430 are removed, and the incision is closed at step 2034 to end the procedure 2000.

It should be understood that the matter contained in the above description and/or shown in the accompanying drawings should be interpreted as illustrative and not in a limiting sense. Those skilled in the art appreciate that variations from the specified embodiments disclosed above are contemplated herein. Certain features and subcombinations are of utility and may be employed without reference to other features and subcombinations and are contemplated within the scope of the claims. Further, various steps set forth herein may be carried out in orders that differ from those set forth herein without departing from the scope of the present methods. The description should not be restricted to the above embodiments, but should be measured by the following claims.

What is claimed is:

1. A system for use in performing spinal surgery, the system comprising:
   at least two threaded caps;
   at least two screw assemblies, each screw assembly comprising:
      a cannulated and threaded screw, the screw having a lower end for threaded engagement in bone and an upper end configured to be engaged by a driving tool;
      a polyaxial head permanently fixed to the screw upper end in a ball-and-socket engagement, the polyaxial head having a receiving area for engaging a rod, the polyaxial head having a threaded area for receiving one of the caps after the rod is engaged in the receiving area such that the rod is sandwiched by the polyaxial head and the cap; and
      an extension portion fixed to the polyaxial head wherein movement of the extension portion causes the polyaxial head to move in concert, the extension portion having first and second arms spaced apart from one another such that the first and second arms are on opposite sides of the polyaxial head receiving area, the extension portion having at least one point of weakness such that forcing the first and second arms away from one another causes the extension portion to divide at the point of weakness and separate the extension portion from the polyaxial head;
   wherein the ball-and-socket engagement allows 360 degree rotation of the polyaxial head about a center axis of the screw and additionally allows the polyaxial head to pivot relative to the screw;
   wherein the first and second arms of the extension portion are sized to extend through skin while the screw is engaged in bone;
   wherein: the first and second arms of the extension portion are configured to pass the rod therebetween while the rod extends in a first direction;
   wherein the polyaxial head is configured to engage the rod in the receiving area while the rod extends in a second direction; and
   wherein the first direction is generally perpendicular to the second direction; and
   a rod insertion tool, the rod insertion tool comprising:
      an elongated housing having upper and lower ends;
      a rotating end pivotably coupled to the housing lower end;
      a first user input device;
      linkage coupling the rotating end to the first user input device to allow at least about ninety degrees of rotation for the rotating end controlled by the first user input device;
      a deformable crown operatively coupled to the rotating end of the rod insertion tool, the deformable crown being biased toward a contracted configuration;
      an actuator movable between first and second positions, the second position being inwardly adjacent the deformable crown and causing the deformable crown to deform to an expanded configuration, the first position allowing the deformable crown to be at the contracted configuration;
      a second user input device; and
      structure coupling the second user input device to the actuator for allowing movement of the actuator between the first and second positions controlled by the second user input device.

2. The system of claim 1, further comprising a salvage tool, the salvage tool comprising:
   two extensions having proximal and distal ends;
   a wall at the distal end of one of the extensions, the wall being configured to extend below one of the polyaxial heads when the two extensions extend alongside the polyaxial head;
   a handle operatively coupled to the two extensions; and
   a trigger in communication with at least one of the extensions for causing the two extensions to be: (a) generally parallel when the trigger is actuated for replicating the first and second arms of the extension portion; and (b) separated further apart from one another when the trigger is released for allowing the extensions to be coupled to and removed from the polyaxial head.

3. The system of claim 2, further comprising a compressor device, the compressor device comprising:
   two arms, each compressor device arm having an attachment portion configured for respective attachment to the extension portions of the screw assemblies; and
   a releasable ratcheting device for selectively imparting a compressive force between the two compressor device arms.

4. The system of claim 3, wherein:
   the two compressor device arms are pivotably attached;
   one of the compressor device arms has a notched indicator, and the other of the compressor device arms has a movable tooth; and
   the movable tooth is interactive with the notched indicator to impart the compressive force between the two compressor device arms.

5. The system of claim 4, further comprising an alignment tool, the alignment tool comprising:
   a rail;
   at least three receiving members coupled to the rail, at least two of the receiving members being movably coupled to the rail, each receiving member having at least one hole for receiving a respective extension portion;
   means for temporarily locking at least one of the receiving members to the rail such that the locked receiving member does not move relative to the rail; and
   means for temporarily locking at least one respective extension portion to one respective receiving member such that the locked extension portion does not move relative to the receiving member.

6. The system of claim 5, further comprising a port, the port comprising:
   a tubular sidewall having upper and lower ends, the tubular sidewall upper end being generally perpendicular to the sidewall, the tubular sidewall lower end being between twenty and forty degrees of being parallel to the tubular sidewall upper end;
   a rim at the tubular sidewall upper end extending outwardly from the diameter of the tubular sidewall; and
   an engagable portion extending upwardly from the rim for attachment to a securing arm.

7. The system of claim 6, wherein the tubular sidewall lower end is about thirty degrees from being parallel to the tubular sidewall upper end.

8. The system of claim 7, further comprising a screwdriver, the screwdriver comprising:

a shaft having an end complementary to the upper ends of the respective screws for driving the screws, the shaft being hollow to allow passage of K-wire; and a guide fixedly coupled to the shaft such that the guide and the shaft rotate in concert, the guide having a plurality of passageways configured to receive the first and second arms of the extension portions.

9. The system of claim 8, further wherein the screwdriver further comprises means for temporarily locking the guide to a respective extension portion.

10. A system for use in performing spinal surgery, the system comprising:

a rod;

at least two threaded caps;

at least two screw assemblies, each screw assembly comprising:

a cannulated and threaded screw, the screw having a lower end for threaded engagement in bone and an upper end configured to be engaged by a driving tool;

a polyaxial head permanently fixed to the screw upper end in a ball-and-socket engagement, the polyaxial head having a receiving area for engaging the rod, the polyaxial head having a threaded area for receiving one of the caps after the rod is engaged in the receiving area such that the rod is sandwiched by the polyaxial head and the cap; and an extension portion fixed to the polyaxial head wherein movement of the extension portion causes the polyaxial head to move in concert, the extension portion having first and second arms spaced apart from one another such that the first and second arms are on opposite sides of the polyaxial head receiving area, the extension portion having at least one point of weakness such that forcing the first and second arms away from one another causes the extension portion to divide at the point of weakness and separate the extension portion from the polyaxial head; and a rod insertion tool, the rod insertion tool comprising:

an elongated housing having upper and lower ends;

a rotating end pivotably coupled to the housing lower end;

a first user input device;

linkage coupling the rotating end to the first user input device to allow at least about ninety degrees of rotation for the rotating end controlled by the first user input device;

a deformable crown operatively coupled to the rotating end of the rod insertion tool, the deformable crown being biased toward a contracted configuration;

an actuator movable between first and second positions, the second position being inwardly adjacent the deformable crown and causing the deformable crown to deform to an expanded configuration, the first position allowing the deformable crown to be at the contracted configuration;

a second user input device; and structure coupling the second user input device to the actuator for allowing movement of the actuator between the first and second positions controlled by the second user input device.

11. The system of claim 10, wherein:

the rod has an imaginary center axis;

the rod has a cavity extending along the imaginary center axis, the cavity only being accessible at an end of the rod; and the rod cavity, the crown, and the actuator are collectively configured such that:

(a) the crown is passable into and out of the rod cavity when at the contracted configuration;

(b) the crown cannot be moved into the rod cavity when at the expanded configuration;

(c) the crown cannot be moved out of the rod cavity when at the expanded configuration; and (d) the crown is alterable between the contracted configuration and the expanded configuration when inside the rod cavity.

\* \* \* \* \*